(12) United States Patent
Sewell et al.

(10) Patent No.: US 8,451,422 B2
(45) Date of Patent: May 28, 2013

(54) RE-FLOW AND BUFFER SYSTEM FOR IMMERSION LITHOGRAPHY

(75) Inventors: Harry Sewell, Ridgefield, CT (US); Erik Theodorus Maria Bijlaart, Rosmalen (NL); Sjoerd Nicolaas Lambertus Donders, Vught (NL); Louis John Markoya, Sandyhook, CT (US); Diane McCafferty, Sandyhook, CT (US); Ralph Joseph Meijers, Kerkrade (NL)

(73) Assignees: ASML Netherlands B.V., Veldhoven (NL); ASML Holding NV, Veldhoven (NL)

( * ) Notice: Subject to any disclaimer, the term of this patent is extended or adjusted under 35 U.S.C. 154(b) by 308 days.

(21) Appl. No.: 12/388,900

(22) Filed: Feb. 19, 2009

(65) Prior Publication Data
US 2009/0213343 A1 Aug. 27, 2009

Related U.S. Application Data

(60) Provisional application No. 61/030,504, filed on Feb. 21, 2008, provisional application No. 61/129,724, filed on Jul. 15, 2008.

(51) Int. Cl.
*G03B 27/52* (2006.01)

(52) U.S. Cl.
USPC .................................. 355/30; 355/67; 355/72

(58) Field of Classification Search
USPC .......................................... 355/30, 67, 72, 77
See application file for complete search history.

(56) References Cited

U.S. PATENT DOCUMENTS

| | | | |
|---|---|---|---|
| 4,509,852 A * | 4/1985 | Tabarelli et al. | 355/30 |
| 4,704,348 A * | 11/1987 | Koizumi et al. | 430/327 |
| 6,714,278 B2 | 3/2004 | Kamiya | |
| 6,952,253 B2 | 10/2005 | Lof et al. | |
| 7,385,673 B2 | 6/2008 | Furukawa et al. | |
| 7,532,306 B2 * | 5/2009 | Dodoc et al. | 355/53 |
| 7,570,343 B2 * | 8/2009 | Dodoc et al. | 355/53 |
| 7,948,603 B2 | 5/2011 | Tanaka | |
| 2001/0050759 A1 | 12/2001 | Kamiya | |
| 2006/0038968 A1 | 2/2006 | Kemper et al. | |
| 2006/0158627 A1 | 7/2006 | Kemper et al. | |
| 2006/0289794 A1 | 12/2006 | Furukawa et al. | |
| 2007/0199201 A1 * | 8/2007 | Tanaka | 34/92 |

(Continued)

FOREIGN PATENT DOCUMENTS

| | | |
|---|---|---|
| EP | 1420298 A2 | 5/2004 |
| EP | 1628163 A2 | 2/2006 |

(Continued)

OTHER PUBLICATIONS

Japanese Office Action dated Aug. 23, 2011 in corresponding Japanese Patent Application No. 2009-037253.

(Continued)

*Primary Examiner* — Thomas R Artman
(74) *Attorney, Agent, or Firm* — Pillsbury Winthrop Shaw Pittman LLP

(57) ABSTRACT

A system is disclosed to isolate an environmental chamber of an immersion lithographic apparatus, to which an immersion fluid comprising liquid, is provided from an external environment. Further, there is disclosed a system for measuring flow rate and/or vapor concentration of a gas using a transducer to send and/or receive an acoustic signal.

29 Claims, 9 Drawing Sheets

U.S. PATENT DOCUMENTS

| | | | |
|---|---|---|---|
| 2008/0106710 A1* | 5/2008 | Lin et al. | 355/30 |
| 2008/0106715 A1* | 5/2008 | Lin et al. | 355/53 |
| 2008/0165335 A1* | 7/2008 | Furukawa et al. | 355/53 |
| 2008/0309894 A1* | 12/2008 | Ehrmann et al. | 355/30 |
| 2009/0213343 A1* | 8/2009 | Sewell et al. | 355/30 |
| 2010/0045952 A1* | 2/2010 | Dodoc et al. | 355/53 |
| 2010/0245789 A1* | 9/2010 | Iwasaki | 355/30 |

FOREIGN PATENT DOCUMENTS

| | | |
|---|---|---|
| JP | 10-209040 | 8/1998 |
| JP | 2000-040659 | 2/2000 |
| JP | 2000-208407 | 7/2000 |
| JP | 2001-167998 | 6/2001 |
| JP | 2002-035668 | 2/2002 |
| JP | 2002-198296 | 7/2002 |
| JP | 2005-101492 | 4/2005 |
| JP | 2005-286358 | 10/2005 |
| JP | 2005-340513 | 12/2005 |
| JP | 2006-134944 | 5/2006 |
| JP | 2006-332146 | 12/2006 |
| JP | 2006-344744 | 12/2006 |
| JP | 2006-344960 | 12/2006 |
| JP | 2007-005714 | 1/2007 |
| JP | 2007-519238 | 7/2007 |
| JP | 2008-034648 | 2/2008 |
| JP | 2008-504708 | 2/2008 |
| WO | 99/49504 A1 | 9/1999 |
| WO | 2007/083686 | 7/2007 |

OTHER PUBLICATIONS

Japanese Office Action mailed Apr. 11, 2012 in corresponding Japanese Patent Application No. 2009-037253.

Japanese Office Action mailed Jan. 30, 2013 in corresponding Japanese Patent Application No. 2009-037253.

* cited by examiner

Fig. 2
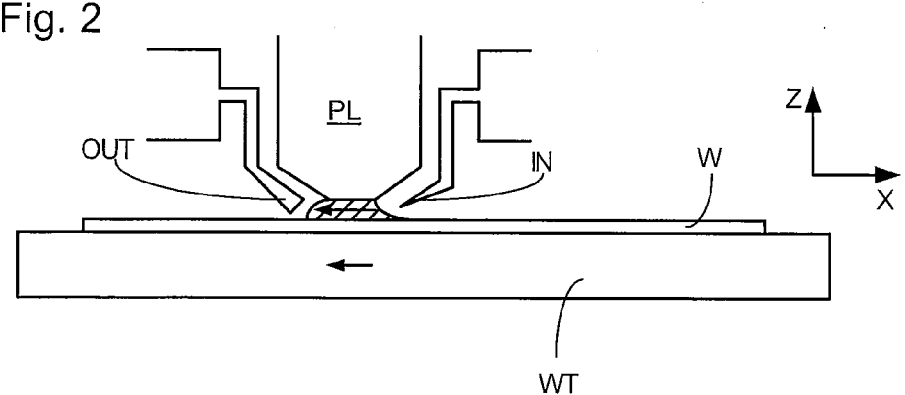
Fig. 3
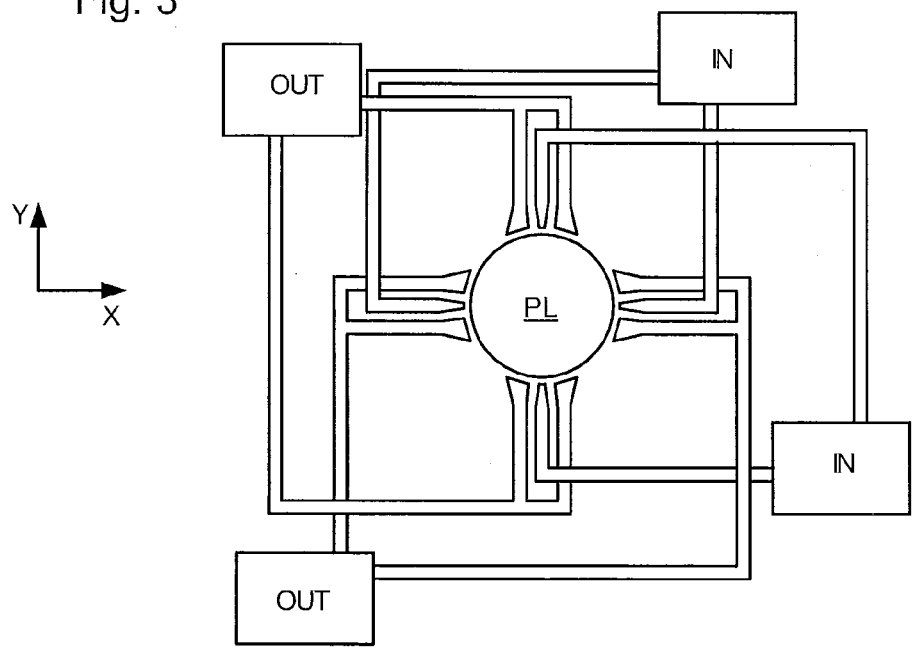
Fig. 4
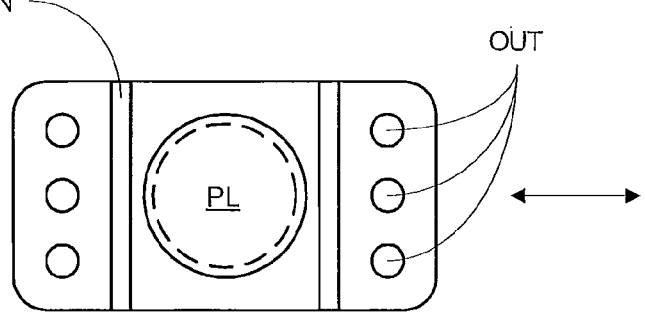
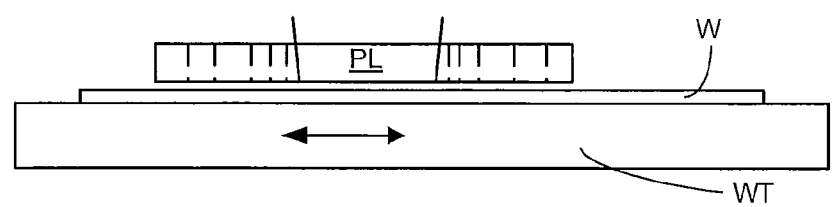

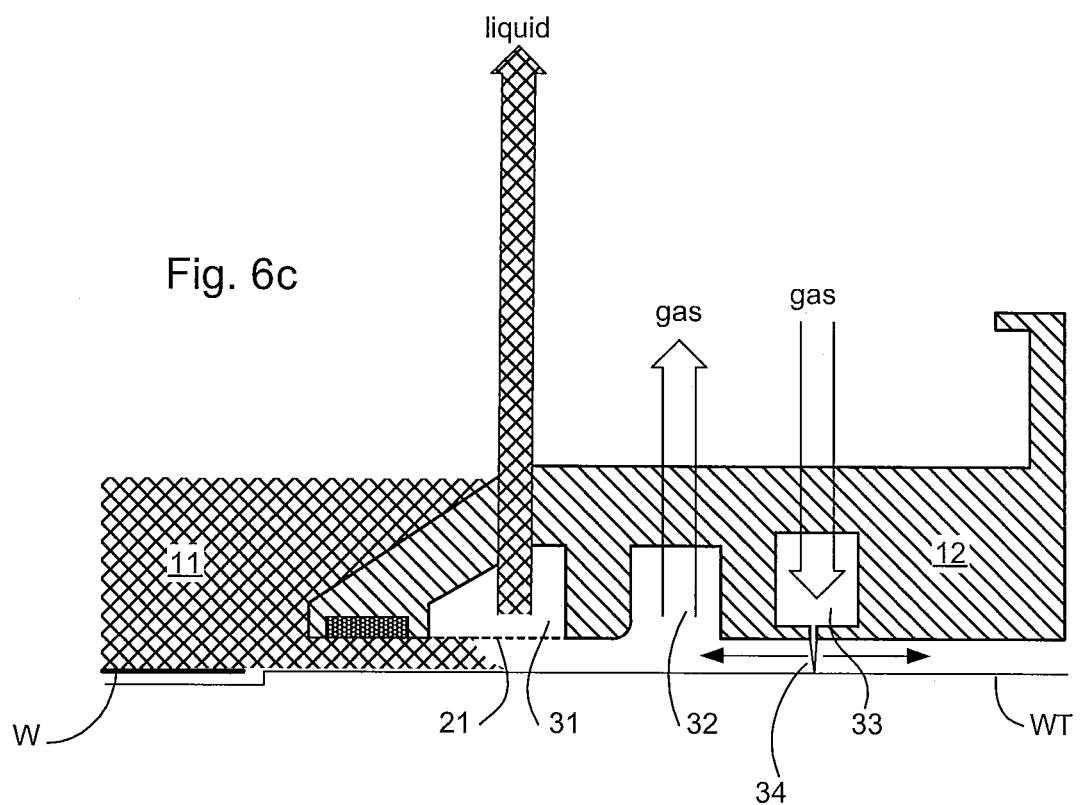

RE-FLOW AND BUFFER SYSTEM FOR IMMERSION LITHOGRAPHY

CROSS-REFERENCE TO RELATED APPLICATIONS

This application claims priority and benefit under 35 U.S.C. §119(e) to U.S. Provisional Patent Application Ser. No. 61/030,504, entitled "Double Walled Protected Flow System For High-N-Immersion Fluid Lithography", filed on Feb. 21, 2008, and to U.S. Provisional Patent Application Ser. No. 61/129,724, entitled "Re-Flow and Buffer System For Immersion Lithography", filed on Jul. 15, 2008. The contents of those applications are incorporated herein in their entirety by reference.

FIELD

The present invention relates to an immersion lithographic apparatus and method of cleaning the immersion lithographic apparatus.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging the pattern using an ultraviolet (UV) radiation beam onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate. Other lithographic apparatus may include interferometric and maskless lithographic patterning devices.

It has been proposed to immerse the substrate in the lithographic projection apparatus in a liquid having a relatively high refractive index, e.g., hydrocarbon liquid, water, etc., so as to fill a space between the final element of the projection system and the substrate. The liquid may be distilled water, although another liquid could be used. The description herein references a liquid. However, another fluid may be suitable, particularly a wetting fluid, incompressible fluid and/or a fluid with a higher refractive index than air, desirably a higher refractive index than water. The point of this is to enable imaging of smaller features since the exposure radiation will have a shorter wavelength in the liquid. (The effect of the liquid may also be regarded as increasing the effective numerical aperture (NA) of the system and also increasing the depth of focus.) Other immersion liquids have been proposed other than water. An organic fluid is one of these liquids being considered. An organic fluid has a higher refractive index than water and typically comprise a hydrocarbon, such as comprising an aromatic group, or a bi-aromatic group, for example decahydronaphthalene (also known as Decalin), a fluorohydrocarbon or a cubane dispersed in an organic solvent. Other proposed immersion liquids, include but are not limited to water with solid particles (e.g., quartz) suspended therein, particles in a fluid having the same or similar refractive index, and dispersed nanoparticles.

Submersing the substrate or substrate and substrate table in a bath of liquid means that there is a large body of liquid that must be accelerated during a scanning exposure. This requires additional or more powerful motors and the resulting turbulence in the liquid may lead to undesirable and unpredictable effects.

One of the solutions proposed is for a liquid supply system to provide liquid on only a localized area of the substrate and in between the final element of the projection system and the substrate using a liquid confinement system (the substrate generally has a larger surface area than the final element of the projection system). A liquid is supplied by at least one inlet IN onto the substrate, desirably along the direction of movement of the substrate relative to the final element, and is removed by at least one outlet OUT after having passed under the projection system. That is, as the substrate is scanned beneath the element in a −X direction, liquid is supplied at the +X side of the element and taken up at the −X side. A liquid is supplied via inlet IN and is taken up on the other side of the element by outlet OUT which is connected to a low pressure source. The liquid is supplied along the direction of movement of the substrate relative to the final element, though this does not need to be the case. Various orientations and numbers of in- and out-lets positioned around the final element are possible. One example is in which four sets of an inlet with an outlet on either side are provided in a regular pattern around the final element.

A twin or dual stage immersion lithography apparatus can be provided with two tables to support a substrate. Leveling measurements are carried out with a table at a first position, without immersion liquid, and exposure is carried out with a table at a second position, where immersion liquid is present. Alternatively, the apparatus has only one table.

As mentioned herein, a fluid such as a hydrocarbon is proposed as the immersion fluid, and has a high refractive index that is greater than existing immersion fluids, such as water.

SUMMARY

The use of a high refractive index fluid, such as hydrocarbon, may require additional environmental control measures in the immersion apparatus. For example, the fluid and vapors may be combustible when mixed with air or oxygen. The fluid may absorb oxygen from the air to increase its absorbency of the exposing radiation. Such a hydrocarbon immersion fluid may degrade under exposure to UV radiation and may leave carbonaceous deposits on critical surfaces, for example, the surface of an optical component. Furthermore, although conventional vapor concentration sensors can measure vapor concentration of water or a specific liquid, they do not have universal applicability. A lag time between measurements by conventional vapor concentration sensors may be significant. In addition, conventional gas flow rate sensors may only measure flow rates of dry gases. Typically conventional gas flow rate sensors are configured for certain types of gases, and do not have universal applicability. Such flow rate sensors may be limited to measuring flow rates in enclosures of specific dimensions.

It is desirable, for example, to provide an immersion lithographic apparatus which reduces one or more of the aforementioned problems, or any other problem not mentioned herein.

According to one embodiment of the present invention, there is provided a lithographic apparatus comprising a projection system, an immersion fluid handling system and an environmental conditioning system. An environmental chamber encloses at least part of a projection system that is configured to project a patterned radiation beam onto a target portion of a substrate, and encloses at least part of the substrate table. The substrate is supported on a substrate table. The immersion fluid handling system is configured to provide an inert gas substantially saturated with immersion liquid vapor to the environmental chamber. The environmental conditioning system may be configured to isolate the environmental chamber from an external environment. The environmental conditioning system may be configured to regulate the atmosphere of a double walled buffer chamber surrounding the environmental chamber and/or confine immersion liquid vapor within the environmental chamber. The environmental conditioning system may confine immersion liquid vapor.

Another embodiment of the present invention provides a method comprising the following steps. Projecting a patterned radiation beam onto a target portion of a substrate using a projection system, the substrate being supported on a substrate table. Providing an immersion liquid to a space between the projection system and the substrate or the substrate table using a liquid supply system. Isolating at least part of the liquid supply system and at least part of the substrate table from an external environment using an environmental conditioning system including an environmental chamber.

A further embodiment of the present invention provides a system for measuring flow rate and vapor concentration of a gas. The system comprises a first transducer configured to transmit a first acoustic signal, a second transducer configured to receive the first acoustic signal, a temperature sensor configured to measure a temperature of a gas between the first and second transducers, and a pressure sensor configured to measure a pressure of the gas. The system also includes control logic configured to measure a first time period between sending and receiving the first acoustic signal and determining a vapor concentration in the gas based on a distance between the first and second transducers, the first time period, the temperature of the gas, and the pressure of the gas.

In an example, the second transducer is configured to transmit a second acoustic signal and the first transducer is configured to receive the second acoustic signal. The control logic is configured to measure flow rate of the gas based on a second time period between sending and receiving the second acoustic signal and the distance between the first and second transducers.

BRIEF DESCRIPTION OF THE DRAWINGS

The accompanying drawings, which are incorporated herein and form a part of the specification, illustrate one or more embodiments of the present invention and, together with the description, further serve to explain the principles of the invention and to enable a person skilled in the pertinent art to make and use the invention.

FIGS. 2 and 3 depict an embodiment of a liquid supply system for use in a lithographic projection apparatus.

FIG. 4 depicts an embodiment of a liquid supply system for use in a lithographic projection apparatus.

FIGS. 6a, 6b and 6c depict an embodiment of a component of a liquid supply system.

One or more embodiments of the present invention will now be described with reference to the accompanying drawings. In the drawings, like reference numbers can indicate identical or functionally similar elements.

DETAILED DESCRIPTION

I. Overview

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention can be implemented in hardware, firmware, software, or any combination thereof. Embodiments of the invention can also be implemented as instructions stored on a machine-readable medium, which can be read and executed by one or more processors. A machine-readable medium can include any mechanism for storing or transmitting information in a form readable by a machine (e.g., a computing device). For example, a machine-readable medium can include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions, etc. can be described herein as performing certain actions. However, it should be appreciated that such descriptions are merely for convenience and that such actions in fact result from computing devices, processors, controllers, or other devices executing the firmware, software, routines, instructions, etc.

II. Example Lithographic Apparatus

Figure 1:
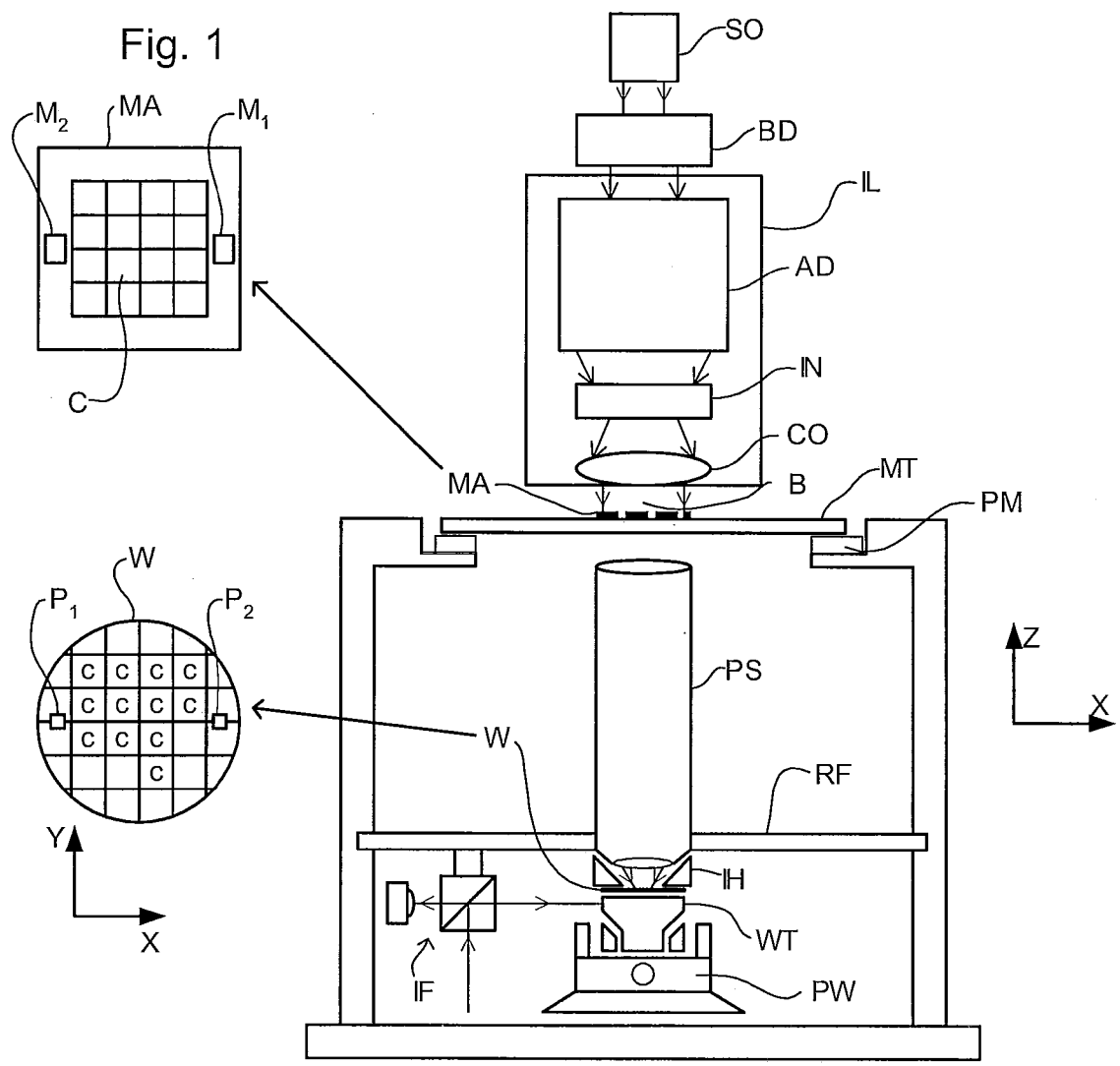
FIG. 1 depicts a lithographic apparatus, according to an embodiment of the invention.

FIG. 1 schematically depicts an embodiment of lithographic apparatus suitable for use with an embodiment of the invention. The apparatus comprises: an illumination system (illuminator) IL configured to condition a radiation beam B (e.g., UV radiation or deep ultraviolet (DUV) radiation); a support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist-coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure MT holds the patterning device. It holds the patterning device in a manner that depends on the orientation of the patterning device, the design of the lithographic apparatus, and other conditions, such as for example whether or not the patterning device is held in a vacuum environment. The support structure MT can use mechanical, vacuum, electrostatic or other clamping techniques to hold the patterning device. The support structure MT may be a frame or a table, for example, which may be fixed or movable as required. The support structure MT may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

Further, in an interferometric lithographic system there is no patterning device, but rather a radiation beam is split into two beams, and the two beams are caused to interfere at a target portion of substrate through the use of a reflection system. The interference causes lines to be formed on at the target portion of the substrate.

The term "projection system" used herein should be broadly interpreted as encompassing any type of projection system, including refractive, reflective, interferometic, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system."

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more patterning device tables). In such "multiple stage" machines the additional tables may be used in parallel, or preparatory steps may be carried out on one or more tables while one or more other tables are being used for exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PS, which focuses the beam onto a target portion C of the substrate W. With the aid of the second positioner PW and position sensor IF (e.g., an interferometric device, linear encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device MA with respect to the path of the radiation beam B, e.g., after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

III. Example Liquid Supply System

An immersion lithography solution with a localized liquid supply system is shown in FIG. 4. Liquid is supplied by two groove inlets IN on either side of the projection system PL and is removed by a plurality of discrete outlets OUT arranged radially outwardly of the inlets IN. The inlets IN and outlets OUT can be arranged in a plate with a hole in its center and through which the radiation is projected. Liquid is supplied by one groove inlet IN on one side of the projection system PL and removed by a plurality of discrete outlets OUT on the other side of the projection system PL, causing a flow of a thin film of liquid between the projection system PL and the projection system PL and removed by a plurality of discrete outlets OUT on the other side of the projection system PL, causing a flow of a thin film of liquid between the projection system PL and the substrate W. The choice of which combination of inlets IN and outlets OUT to use can depend on the direction of movement of the substrate W (the other combination of inlet IN and outlets OUT being inactive).

Figure 5:
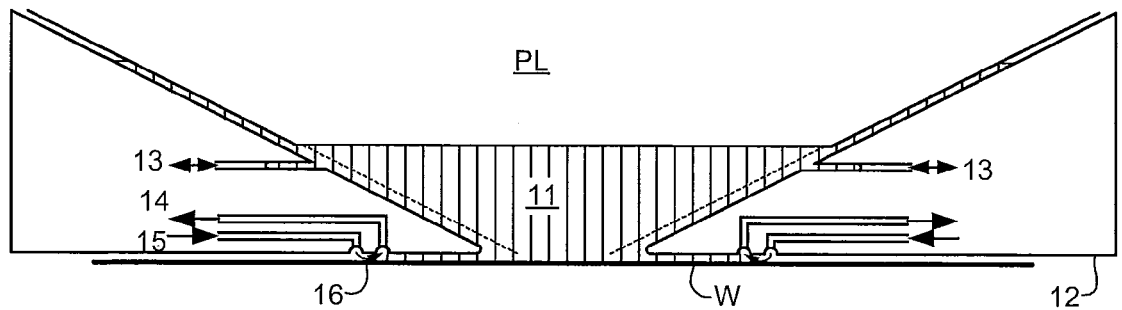
FIG. 5 depicts an embodiment of a liquid supply system.

Another immersion lithography solution with a localized liquid supply system solution which has been proposed is to provide the liquid supply system with a barrier member (or so-called immersion hood), which extends along at least a part of a boundary of the space between the final element of the projection system and the substrate table, the substrate W or both. Such a solution is illustrated in FIG. 5. The barrier member is substantially stationary relative to the projection system in the XY plane though there may be some relative movement in the Z direction (in the direction of the optical axis). A seal may be formed between the barrier member and the surface of the substrate, the substrate table or both. Reference to substrate hereinafter includes the substrate W or the substrate table WT or both, unless expressly stated otherwise. Desirably the seal is a contactless seal such as a gas seal.

Referring to FIG. 5, a barrier member 12 forms a contactless seal to the substrate around the image field of the projection system so that liquid is confined to fill a reservoir or an immersion space 11 between the substrate surface and the final element of the projection system. The reservoir 11 is formed by a barrier member 12 positioned below and surrounding the final element of the projection system PL. Liquid is brought into the space below the projection system and within the barrier member 12 through, for example, opening 13. The barrier member 12 extends a little above the final element of the projection system and the liquid rises above the final element so that a buffer of liquid is provided. The barrier member 12 has an inner periphery that at the upper end, in an embodiment, closely conforms to the shape of the projection system or the final element thereof and may, e.g., be round. At the bottom, the inner periphery closely conforms to the shape of the image field, e.g., rectangular though this need not be the case.

The liquid is confined in the reservoir by a gas seal 16 between the bottom of the barrier member 12 and the surface of the substrate W. The gas seal is formed by gas, e.g., air or synthetic air but, in an embodiment, $N_2$ or an inert gas, provided under pressure via inlet 15 to the gap between barrier member 12 and substrate and extracted via outlet 14. The overpressure on the gas inlet 15, vacuum level on the outlet 14 and geometry of the gap are arranged so that there is a high-velocity gas flow inwards that confines the liquid. An exemplary system is disclosed in U.S. Pat. No. 6,952,253, which is incorporated herein by reference in its entirety.

Other solutions are possible and one or more embodiments of the present invention are equally applicable to those. For example, in place of the gas seal 16 it is possible to have a single phase extractor which only extracts liquid. Radially outwardly of such a single phase extractor could be one or more features to produce a gas flow to help contain the liquid in the space. One such type of feature might be a so-called "gas knife" 34 (see FIG. 6C) in which a thin jet of gas is directed downwards onto the substrate W. During scanning motion of the substrate under the projection system and the liquid supply system, hydrostatic and hydrodynamic forces may be generated which result in pressures on the liquid downwards towards the substrate.

With a localized area liquid supply system, the substrate W is moved under the projection system PL and the liquid supply system. The relative movement of the substrate table WT may enable an edge of the substrate W to be imaged or a sensor on the substrate table WT to be imaged for sensing purposes or for substrate swap. Substrate swap is removal and replacement of the substrate W from the substrate table WT between exposures of different substrates. During substrate swap it may be desirable for liquid to be kept within the liquid confinement system 12. This may be achieved by moving the liquid confinement system 12 relative to the substrate table WT, or vice versa, so that the liquid confinement system is placed over a surface of the substrate table WT away from the substrate W. Such a surface is a shutter member. Immersion liquid may be retained in the liquid confinement system by operating the gas seal 16 or by clamping the surface of the shutter member to the undersurface of the liquid confinement system 12. The clamping may be achieved by controlling the flow and/or pressure of fluid provided to the undersurface of the liquid confinement system 12. For example, the pressure of gas supplied from the inlet 15 and/or the under pressure exerted from the outlet 14 may be controlled.

The surface of substrate table WT over which the liquid confinement system 12 is placed may be an integral part of the substrate table WT or it may be a detachable and or replaceable component of the substrate table WT. Such a detachable component may be referred to as closing disc or a dummy substrate. The detachable or separable component may be a separate stage. In a dual or multi stage arrangement the entire substrate table WT is replaced during substrate exchange. In such an arrangement the detachable component may be transferred between substrate tables. The shutter member may be an intermediate table that may be moved adjacent to the substrate table WT prior to substrate exchange. The liquid confinement system may then be moved onto the intermediate table, or vice versa during substrate exchange. The shutter member may be a moveable component of substrate table WT, such as a retractable bridge, which may be positioned between the stages during substrate exchange. The surface of the shutter member may be moved under the liquid confinement system 12, or vice versa, during substrate exchange.

During substrate swap, an edge of the substrate W will pass under the space 11 and liquid may leak into the gap between the substrate W and substrate table WT. This liquid may be forced in under hydrostatic or hydrodynamic pressure or the force of a gas knife or other gas flow creating device. A drain may be provided around the edge of a substrate W, such as in the gap between substrate W and substrate table WT. A drain may be located around another object on substrate table WT. Such an object may include, but is not limited to, one or more sensors and/or a shutter member used to maintain liquid in the liquid supply system by being attached to the bottom of the liquid supply system during, for example, substrate swap. Thus, any reference to the substrate W should be considered to be synonymous with any such other object, including a sensor or shutter member, such as a closing plate.

For other exemplary lithographic systems, see generally U.S. Pat. No. 4,509,852, PCT Patent Application Publication No. WO 99/49504, and European Patent Application Publication No. EP-A-1,420,298, which are all incorporated by reference herein in their entireties.

Figure 6A:
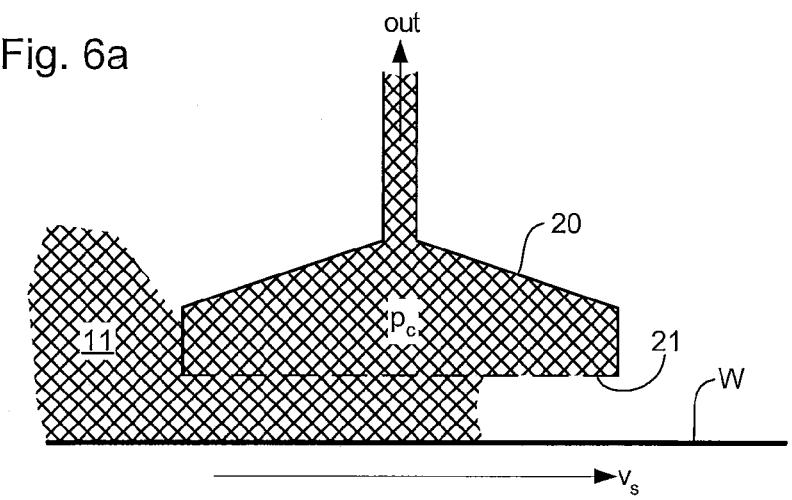
Figure 6B:
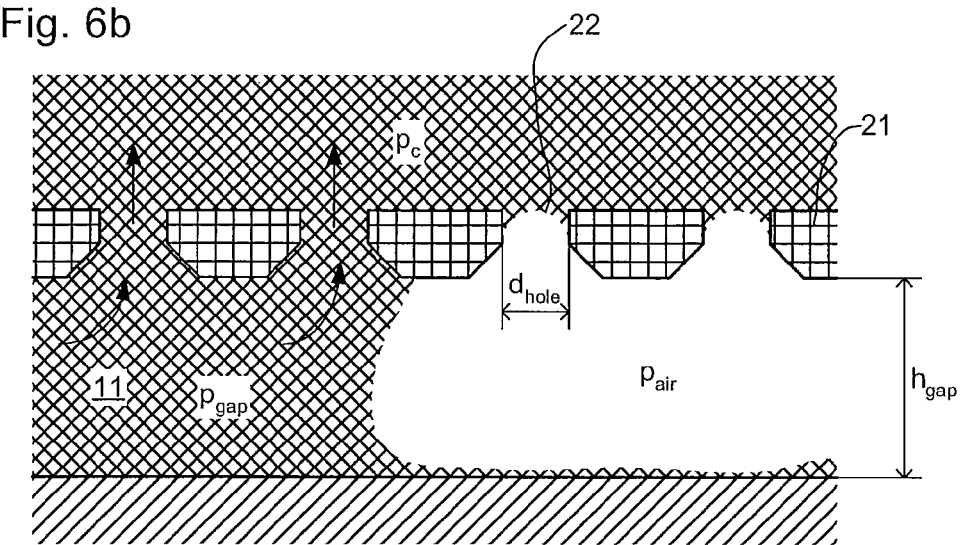

FIG. 6a illustrates a liquid removal device 20, of a liquid handling structure 12, which may be used in immersion systems to remove liquid between the immersion hood IH and the substrate W. FIG. 6b is an enlarged view of FIG. 6a. The liquid removal device 20 comprises a chamber which is maintained at a slight underpressure $p_c$ and is filled with the immersion liquid. The lower surface of the chamber is formed of a porous member 21 having a plurality of small holes, e.g., of diameter $d_{hole}$ in the range of about 5 to 50 μm, and is maintained at a height $h_{gap}$ less than about 1 mm, desirably in the range of about 50 to 300 μm above a surface from which liquid is to be removed, e.g., the surface of a substrate W. The porous member 21 may be a perforated plate or any other suitable structure that is configured to allow the liquid to pass there through. In an embodiment, porous member 21 is at least slightly liquidphilic, i.e. having a contact angle of less than 90° to the immersion liquid, e.g. water.

Such liquid removal devices can be incorporated into many types of barrier member 12 and immersion hood IH. One example is illustrated in FIG. 6c as disclosed in U.S. Patent Application Publication No. 2006-0038968, which is incorporated by reference herein in its entirety.

FIG. 6c illustrates a cross-sectional view of one side of the barrier member 12, which forms a ring (as used herein, a ring may be circular, rectangular or any other shape and it may be continuous or discontinuous) at least partially around the exposure field of the projection system PL (not shown in FIG. 6c). In this embodiment, the liquid removal device 20 is formed by a ring-shaped chamber 31 near the innermost edge of the underside of the barrier member 12. The lower surface of the chamber 31 is formed by a porous member, such as the porous member described above. Ring-shaped chamber 31 is connected to a suitable pump or pumps to remove liquid from the chamber and maintain the desired underpressure. In use, the chamber 31 is full of liquid but is shown empty here for clarity.

Outward of the ring-shaped chamber 31 may be a gas extraction ring 32 and a gas supply ring 33. The gas supply ring 33 may have a narrow slit in its lower part and is supplied with gas, e.g., air, artificial air or flushing gas, at a pressure, such that the gas escaping out of the slit forms a gas knife 34. The gas forming the gas knife is extracted by a suitable vacuum pump connected to the gas extraction ring 32 so that the resulting gas flow drives residual liquid inwardly where it can be removed by the liquid removal device 20 and/or the extraction ring 32, which should be able to tolerate vapor of the immersion liquid and/or small liquid droplets. However, since the majority of the liquid is removed by the liquid removal device 20, the small amount of liquid removed via the extraction ring 32 does not cause unstable flows which may lead to vibration.

While the chamber 31, gas extraction ring 32, gas supply ring 33 and other rings are described as rings herein, it is not necessary that they surround the exposure field or be complete. They may be continuous or discontinuous. In an embodiment, such inlet(s) and outlet(s) may simply be any annular shape such as circular, rectangular or other type of elements extending partially along one or more sides of the exposure field, such as for example, shown in FIGS. 2, 3 and 4.

In the apparatus shown in FIG. 6c, most of the gas that forms the gas knife is extracted via gas extraction ring 32, but some gas may flow into the environment around the immersion hood IH and potentially disturb the interferometric position measuring system IF. This can be prevented by the provision of an additional gas extraction ring outside the gas knife (not shown).

Further examples of how such single phase extractors can be used in a liquid confinement system or liquid supply system can be found, for example, in European Patent Application Publication No. EP 1628163, U.S. Patent Application No. U.S. 60/643,626 and U.S. Patent Application Publication No. US 2006-0158627, which are all incorporated by reference herein in their entireties. In most applications, the porous member will be on an underside of the liquid supply system and the maximum speed at which the substrate W can move under the projection system PS is at least in part determined by the efficiency of removal of liquid through the porous member 21.

A single phase extractor can be used in two phase mode in which both liquid and gas are extracted (e.g., about 50% gas, 50% liquid). The term single phase extractor is not intended herein to be interpreted only as an extractor that extracts one phase, but more generally as an extractor which incorporates a porous member through which gas and/or liquid is/are extracted. In an embodiment of the gas knife 34, the gas supply ring 33 may be absent.

The above mentioned single phase extractor can be used in liquid supply systems that supply liquid to only a localized area of the top surface of the substrate. Furthermore, such an extractors can be used in other types of immersion apparatus. Also, the extractor can be used for an immersion liquid other than water. The extractor can be used in a so-called "leaky seal" liquid supply system. In such a liquid supply system, liquid is provided to the space between the final element of the projection system and the substrate. That liquid is allowed to leak from that space radially outwardly. For example, an immersion hood IH or liquid confinement system 12 or liquid supply system (FIGS. 3 and 4) is used, which does not form a seal between itself and the top surface of the substrate W or substrate table WT, as the case may be. The immersion liquid may only be retrieved radially outwardly of the substrate in a "leaky seal" apparatus.

The comments made in relation to a single phase extractor may apply to other types of extractor, for example an extractor without a porous member. Such an extractor may be used as a two phase extractor to extract one or both of liquid and gas.

Embodiments of the present invention will be described in relation to a lithographic apparatus having an immersion system with a liquid handling system and drain as described in the aforementioned figures. However, it will be apparent that the embodiments can be applied to any sort of immersion apparatus. The systems and components described in the earlier passages of the description are thus example systems and components. The embodiments may apply to other features of the immersion system which include, but are not limited to, cleaning systems and cleaning tools for in-line and off-line implementations; liquid supply and liquid retrieval systems such as an ultra pure water supply and/or retrieval system, and gas supply and removal systems (e.g., a vacuum pump).

The embodiments will be described below in relation to an immersion system optimized for supplying an immersion liquid. However, the embodiments are equally applicable for use with an immersion system that uses a fluid supply system supplying a fluid other than a liquid as the immersion medium.

IV. Example Flow System for a Lithographic Apparatus

Figure 7:
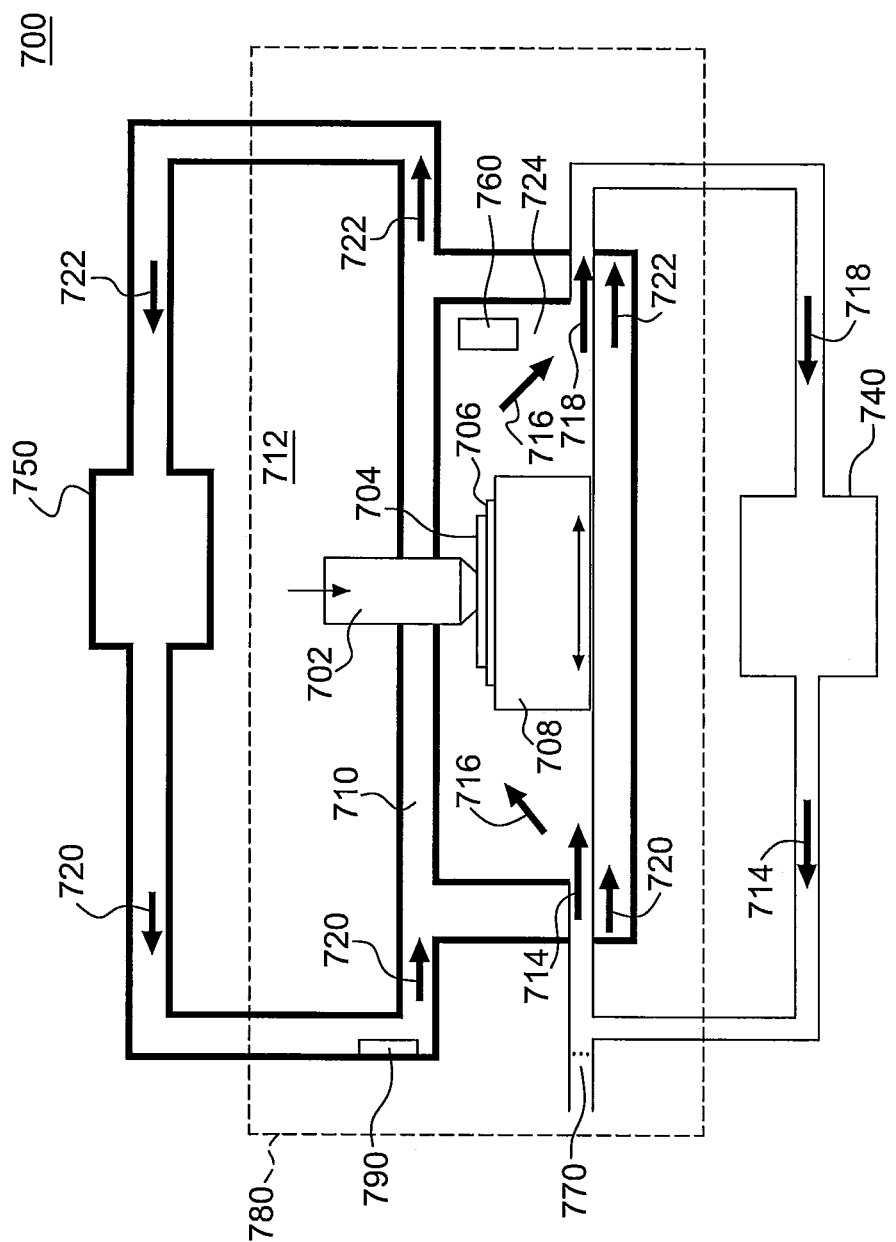
FIG. 7 is a schematic diagram of an exemplary flow and buffer system for a lithographic apparatus according to an embodiment of the present invention.

FIG. 7 illustrates an apparatus 700 according to an embodiment of the present invention. Apparatus 700 includes an enclosure 780 that encloses optical system 702, a substrate 706 and a substrate table 708 configured to support and move a substrate 706 relative to the projection system 702, immersion liquid 704 confined between a final element or portion of the optical system 702 and the substrate 706. In another example, the immersion liquid 704 is supplied to flow over the surface of the substrate 706, for example the whole of the substrate surface, and the liquid 704 is not confined. In such an immersion system, the liquid confinement structure may be as previously described, but the immersion liquid extractors and/or a gas seal, for example, do not exist or are non-operational.

Apparatus 700 includes an immersion fluid handling system (not identified) that comprises an immersion liquid handling structure as described above (see FIGS. 2 to 6), a reflow system 740, metrology and control system 760 and environmental chamber 724. Apparatus 700 also includes an environmental conditioning system (not identified) that includes buffer system 750, buffer chamber 710 and metrology and control system 790. The buffer chamber 710 (which may be double walled) isolates environmental chamber 724 from external atmosphere 712. Load lock 770 provides a substrate track (not shown) access to environmental chamber 724. The substrate track supplies substrates 706 to substrate table 708. In an embodiment, enclosure 780 may enclose in part or in entirety, immersion fluid handling system, environmental conditioning system, optical system 702 and substrate table 708. In an embodiment, external atmosphere 712 is internal to enclosure 780. In an embodiment, external atmosphere 712 may be external to enclosure 780. The apparatus 700 can comprise an immersion lithography apparatus as previously described, which is adapted to use an immersion liquid 704 with a refractive index higher than water, for example, a hydrocarbon, desirably a hydrocarbon with an aromatic function group or even a bi-aromatic group such as Decalin. In an embodiment, substrate table 708 may be table WT and substrate 706 may be substrate W.

In an immersion lithographic apparatus, the environment above the substrate during exposure may be regulated by a controlled flow of gas. The gas may have a regulated temperature and/or may be filtered. The gas flow may control and regulate the temperature of the gaseous environment around the substrate and the immersion system. However, when a liquid with a higher refractive index than water is used, such as a hydrocarbon, there is a risk that oxygen may dissolve into the immersion liquid. One risk is that the immersion liquid may evaporate, for example as a consequence of the gas flow. The gas flow may transport the immersion liquid. The gas flow may distribute the immersion liquid around the lithographic apparatus. The immersion liquid may be flammable, and/or noxious (poisonous), which may cause a health hazard and/or environmental risk using the immersion system of a known lithographic apparatus. Further, interaction of the immersion liquid with UV radiation may cause damage to the lithographic apparatus. Such interaction could cause unwanted carbonaceous deposits on a surface of the lithographic apparatus. The deposit may damage a component of the apparatus, for example, an optical component or sensor. Also, the deposit may be a potential source of a risk of later damage of the lithographic apparatus.

Thus, apparatus 700 includes double-walled buffer chamber 710. The chamber 710 acts as a buffer, preventing or reducing the risk of immersion liquid 704 escaping in liquid or vapor form from environment chamber 724 into an environment 712 surrounding the lithographic apparatus 700, especially its immersion system. The chamber 710 may prevent or reduce the risk of ingress of oxygen into the environmental chamber 724 and help prevent it from being absorbed by the immersion liquid 704. The chamber 710 isolates the environmental chamber 724 from an external environment 712.

The environmental chamber 724 may be connected to a substrate track system (not shown) that supplies substrates 706 to the apparatus 700 via load lock 770. Load lock 770 may be a gas curtain or a gas knife 34 as described above with reference to FIG. 6c. The atmosphere 716 within the chamber 724, which comes into contact with the immersion liquid 704, may comprise an inert (non reactive) gas 714, such as nitrogen ($N_2$), which may be about 100% saturated with immersion liquid vapor. Thus, the atmosphere 716 within chamber 724 may comprise a near saturated level of vapor of the immersion liquid 704. The level of the vapor (i.e., the vapor pressure of the immersion liquid 704) in the atmosphere 716 may be maintained at the near saturated level. The level may be a certain threshold.

In an embodiment, metrology and control system 760 is configured to monitor temperature, flow rate, pressure and/or vapor saturation of gas in environmental chamber 724. In an embodiment, metrology and control system 760 is configured to control reflow system 740 to adjust the temperature, flow rate, pressure and/or vapor saturation levels of gas in environmental chamber 724 based on measurements made by metrology and control system 760 and certain/dynamically programmed thresholds. In one example, metrology and control system 760 and/or metrology and control system 790 include a flow rate and vapor concentration measurement system 1000 (see FIG. 10) for measurement of flow rate and/or vapor concentration of a gas.

In an embodiment, metrology and control system 760 is located inside environmental chamber 724, proximate to the substrate 704. Alternatively or additionally, the metrology and control system 760 may be located away from the substrate table WT when it is located underneath the projection system 702, for example with a second stage of a dual stage embodiment at a measuring station, or associated with a measurement table.

The gas 714 of the atmosphere 716 may be filtered by reflow system 740, for example to remove particulates. The temperature of the gas 714 may be maintained and regulated within a certain range. The range may be small and have very tight limits. The chamber 710 and the gas flow through the chamber 710 may be arranged to exclude oxygen from the enclosed and controlled environment 716. Similar to metrology and control system 760, metrology and control system 790 is configured to monitor temperature, flow rate, pressure and/or vapor saturation of gas in buffer chamber 710. In an embodiment, metrology and control system 790 is configured to control buffer system 750 to adjust the temperature, flow rate, pressure and/or vapor saturation levels of gas in buffer chamber 710 based on certain thresholds or dynamically programmed thresholds. In an embodiment, any immersion vapors in buffer chamber 710 are condensed using condenser 904 (see FIG. 9). In an embodiment, metrology and control system 790 is located inside buffer chamber 710. It is to be appreciated that the location of metrology and control system 790 inside buffer chamber 710 is a design choice and may be arbitrary.

As shown in FIG. 7, the gas 714 in the atmosphere 716 can be re-circulated and/or reclaimed as gas 718. The atmosphere 716 comprising an inert gas 714, such as nitrogen, and substantially saturated with vapor of the immersion liquid 704 is supplied to the chamber 710. The gas flows past the immersion system of the lithographic apparatus 700 where it is removed. The removed gas 718 is supplied to a recirculation or reflow system 740. In the reflow system 740, the gas may be filtered, temperature conditioned, and/or conditioned with vapor of the immersion liquid based on measurements made by metrology and control system 760. Once reconditioned, the gas may be re-supplied to the environmental chamber 710. Buffer system 750 is described in further detail below with reference to FIG. 8.

The buffer chamber 710 may enclose the substrate table 708 (including the substrate stage and sensors which may be located on the substrate table 708), the immersion fluid handling system which may include reflow system 740, a metrology and control system 760 and its associated detectors, and a liquid handling structure (see FIGS. 2 to 6). In one example, a load lock 770 may be provided between the track system and the lithographic apparatus 700. The load lock 770 may be operated on supplying a substrate into the immersion system of the lithographic apparatus. The load lock 770 may operate on removing the substrate. The load lock 770 may be an opening (e.g. a doorway) providing access into and out of the environment chamber 724. A load lock can be a gas curtain (e.g. a gas knife 34) rather than a physical closure device, such as a door. However, the gas curtain should be sufficient for keeping the atmosphere of the environmental chamber 724 separate from the surrounding external atmosphere 712.

In this example, the environmental chamber 724 is isolated by buffer chamber 710 that allows buffer gas 720 to flow in and buffer gas 722 to flow out, for example to a buffer system 750, particularly any region of the lithographic apparatus 700 which may be exposed to UV illumination. Reflow system 740 is described in further detail below with respect to FIG. 9.

Any hydrocarbon fumes or vapors, even in parts per billion, will be degraded by the UV illumination to produce carbonaceous deposits. The buffer chamber 710 may be a guard against the formation of such deposits. The environmental conditioning system may have its own load locks between the external atmosphere 712 and the buffer chamber 710 and environmental chamber 724.

In this example, double-walled buffer chamber 710 isolates environmental chamber 724 from external atmosphere 712. Within the buffer chamber 710 is buffer gas flow 720/722. The buffer gas flow 720/722 is a separate flow of inert gas 714/718, which may include nitrogen or air. The inert gas 714/718 purges the buffer chamber 710. The buffer chamber 710 is effectively a double walled zone between the environmental chamber 724 and external atmosphere 712. It buffers the environmental chamber 724 with respect to the temperature control, the oxygen exposure of the immersion liquid 704, and the escape of immersion liquid vapor into the surrounding atmosphere 712. The gas flow 720/722 through the buffer chamber 710 can be filtered by buffer system 750 to remove particulates, temperature regulated and/or conditioned to remove immersion liquid vapor.

Additionally, or alternatively, the environmental conditioning system may have further chambers (not specifically shown) surrounding the buffer chamber 710, which may be arranged in a generally concentric manner. Each chamber may add a further wall to the arrangement. So that an environmental conditioning system with three concentric buffer chambers is a four walled arrangement. The more concentric buffer chambers an environmental conditioning system has, the more effective and efficient the environmental conditioning system is, but the more costly and complicated the system is to implement.

In an embodiment, a substrate 706, which has applied to at least part of its surface an immersion liquid 704 to wet the surface, is located in a controlled gaseous environment 716. The environment 716 in the environmental chamber 710 is generally controlled by the high level of vapor saturation so that the rate of evaporation and associated cooling is significantly reduced. The arrangement may control the liquid vapor that is captured and re-circulated. For example, oxygen is excluded from the region of the substrate and liquid handling system. The risk of oxidation of the immersion liquid and vapor, and even its combustion, may be thus reduced. This helps reduce the chance of deposits of oxidized immersion liquid forming in the immersion system and helps to prevent the formation of imaging defects. So any reaction of the vapor with a gas 720 in its immediate environment may be prevented, or at least substantially reduced. The number and size of defects caused during scanning may be reduced. Filtering the gas 720 for particles may reduce defects in size and number.

The arrangement may control the temperature of the buffer gas 720, i.e., the inert gas. This environmental control impacts the immersion liquid evaporation rate from a substrate 706, substrate table 708 and stage. The operation of the environmental control is directly related to, and thus helps achieve, control of overlay within acceptable tolerances.

In one example, the buffer chamber 710 uses buffer system 750 for nitrogen gas 720. The buffer system 750 is compact and local to the surface of substrate table 708 (substrate stage) and/or sensor region (not shown). Such a sensor region may be a location for an encoder (not shown). The buffer system 750 economically controls the gas usage because it is recirculating. Its use can maintain precise control over the evaporation rate of the immersion liquid 704, and hence temperature control of the substrate 706. This control helps improve overlay performance of the lithographic apparatus. The use of an inert gas 720 such as nitrogen helps prevent degradation of the immersion liquid 706, e.g., a high refractive index immersion liquid, by oxidation which could produce defects on a substrate 706. Such a defect could be caused by oxidized deposits such as a skin or a gelatinous deposit.

In the embodiments discussed above, the double-walled flow design buffers the external atmosphere 712 from the environmental chamber 724 to improve performance and safety. The environmental chamber 724 is isolated from the external atmosphere 712. Use of an inert gas such as nitrogen substantially prevents contamination of the high refractive index immersion liquid by, for example, oxygen or water vapor. The exclusion of oxygen substantially prevents any possible combustion of a flammable immersion liquid, such as a hydrocarbon liquid. The double walled system may prevent the escape of high refractive index vapors, which could condense on sensitive components inside the lithography tool, such as energy and position sensors and illumination optics.

V. Reflow System

Figure 8:
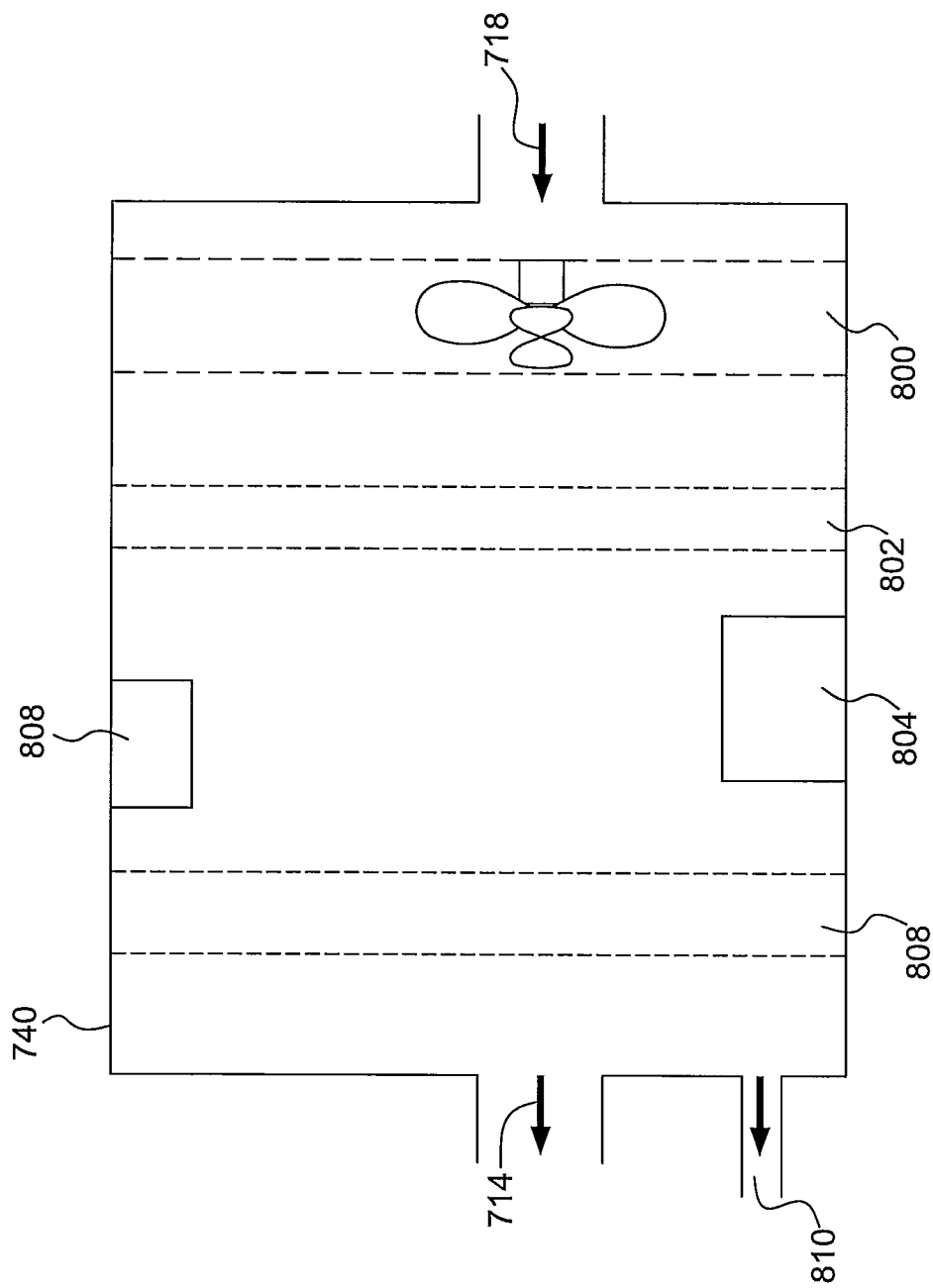
FIG. 8 illustrates a reflow system according to an embodiment of the invention.

FIG. 8 illustrates reflow system 740, according to an embodiment of the invention. Reflow system 740 includes, but is not limited to, a blower unit 800, a humidifier membrane 802, a condenser 804, a flow particle filter 806, a heat exchanger 808 and a make-up gas input 810.

Figure 10:
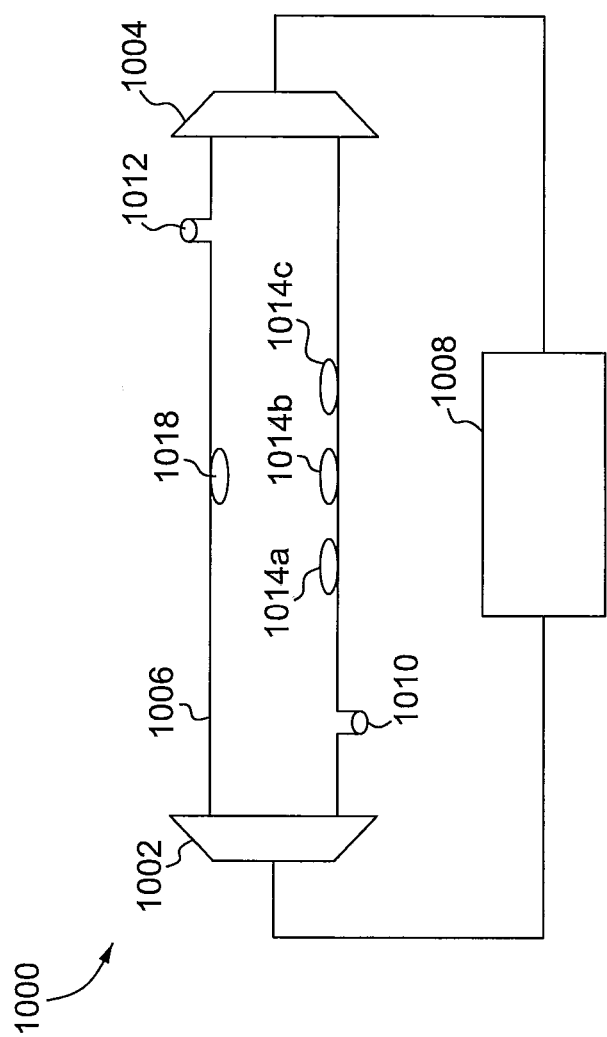
FIG. 10 illustrates a flow rate and vapor concentration measurement system according to an embodiment of the invention.

Blower unit 800 may include a fan configured to control flow rate of gas through environmental chamber 724 based on flow rate measurements made by flow rate and vapor concentration measurement system 1000 (see FIG. 10). In an embodiment, if metrology and control system 760 determines that the flow rate of gas through environmental chamber 724 is lower than a certain threshold or a certain range of flow rates, then metrology and control system 760 increases or decreases the fan speed of blower unit 800 to compensate for the change in flow rate.

In an embodiment, flow rate and vapor concentration measurement system 1000 may determine vapor concentration of immersion liquid 704 in reflow system 740. Humidifier membrane 802 is configured to impart the gas flowing through reflow system 740 with vapor of immersion liquid 704 if measurements by flow rate and vapor concentration measurement system 1000 indicate vapor concentration of immersion liquid 704 to be below a certain level. Humidifier membrane 802 may be semi-permeable humid membrane. Gas flowing through humidifier membrane 802 absorbs vapor of immersion liquid 704. Additionally, or alternatively, humidifier membrane 802 may comprise hollow fibrous micro-tubes or nano-tubes. As can be appreciated, other devices may also be used for membrane 802. Reflow system 740 is configured to adjust the humidity level of membrane 802 based on vapor saturation levels as measured by flow rate and vapor concentration measurement system 1000. In various examples, the saturation level may be certain or may be changed dynamically by programming metrology and control system 760. Based on the specified saturation level and measurements by flow rate and vapor concentration measurement system 1000, metrology and control system 760 may control the humidity level of membrane 802 and thereby the vapor saturation level of gas through environmental chamber 724.

Condenser 804 may be configured to condense vapor of immersion liquid 704 if the vapor concentration levels as measured by flow rate and vapor concentration measurement system 1000 exceeds a certain level. Condenser 804 may include a drain configured to drain the condensed vapor. In an embodiment, condenser 804 uses UV radiation in conjunction with oxygen radicals to breakdown hydrocarbon into water and carbon monoxide. UV radiation, typically at wavelengths less than 194 nm, is used to induce the following chemical reaction:

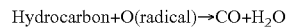

$$\text{Hydrocarbon} + \text{O(radical)} \rightarrow \text{CO} + \text{H}_2\text{O}$$

A source of oxygen (not shown) in conjunction with UV radiation is used to supply activated oxygen radicals, which react with hydrocarbon and carbon based compounds in vapor of immersion liquid 704. The oxygen radicals convert the hydrocarbon into water and an oxide of carbon. A UV lamp may be used to supply the UV radiation. Buffer system 750 may also employ the UV lamp and oxygen source to decompose unwanted hydrocarbon fumes that result from the use of hydrocarbon high refractive index immersion liquid 704.

Flow particle filter 806 may be configured to filter particles in the gas flowing through reflow system 740. In an embodiment, flow particle filter 806 filters particles of size about 30 nm and higher.

Reflow system 740 may also include a heat exchanger 808 configured to adjust temperature of a gas flowing through reflow system 740 if temperature readings by metrology and control system 760 indicate that the temperature of the gas flowing through environmental chamber 724 is above or below a certain temperature or range of temperatures.

Reflow system 740 may also include a make-up gas input 810 to supply inert gas to reflow system 740. In an embodiment, metrology and control system 760 detects a change in gas pressure due to, for example, leakage via load lock 770. Metrology and control system 760 may be configured to control make-up gas input 810 to supply gas based on measurements of gas pressure in environmental chamber 724.

VI. Buffer System

Figure 9:
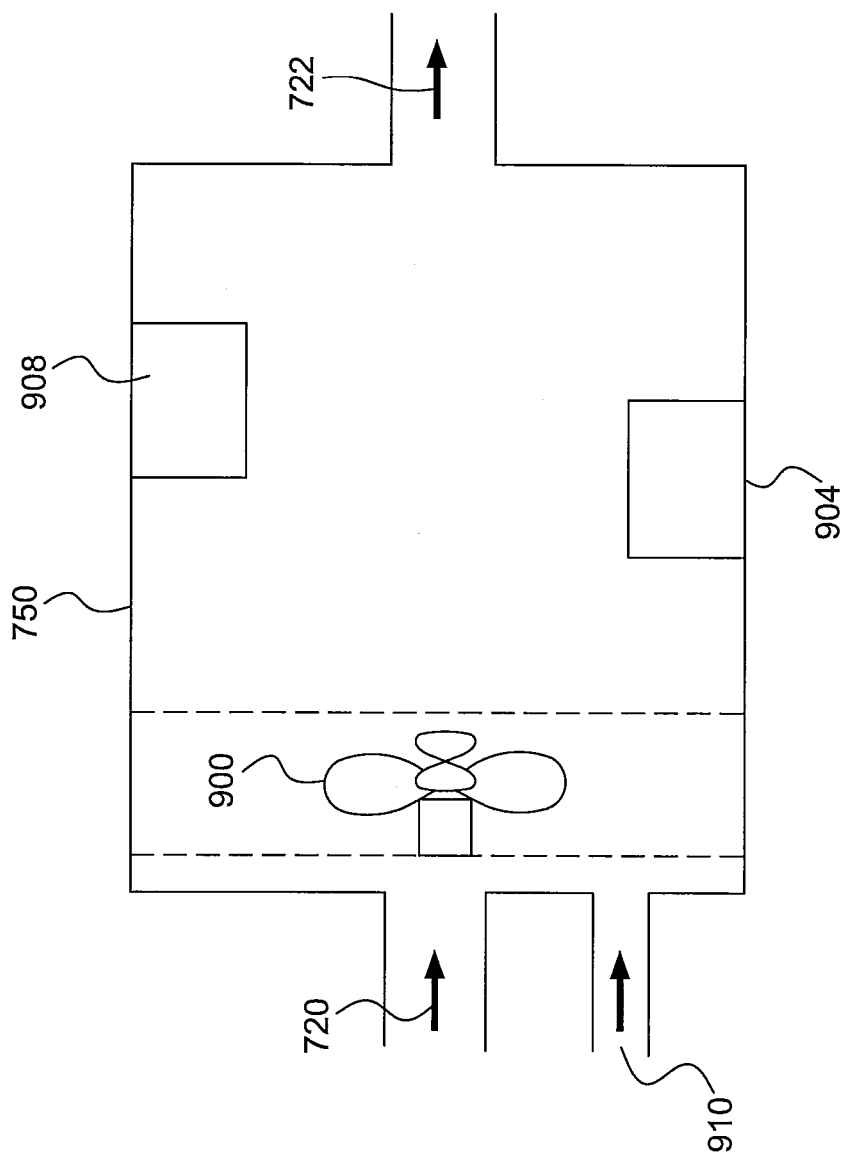
FIG. 9 illustrates a buffer system according to an embodiment of the invention.

FIG. 9 illustrates buffer system 750, according to an embodiment of the invention. Buffer system 750 may include, but is not limited to, a blower unit 900, condenser 904, heat exchanger 908 and make-up gas input 910.

Blower unit 900 may include a fan configured to control flow rate of gas through buffer chamber 710 based on flow rate measurements made by flow rate and vapor concentration measurement system 1000. In an embodiment, if flow rate and vapor concentration measurement system 1000 determines that the flow rate of gas through buffer chamber 710 is slower than a certain threshold or a certain range of flow rates, then metrology and control system 790 increases or decreases the fan speed of blower unit 900 to compensate for the change in flow rate. In an embodiment, metrology and control system 790 is configured to the flow rate through buffer chamber 710 based on the flow rate in environmental chamber 724 as measured by metrology and control system 760.

Condenser 904 may be configured to condense immersion liquid 704 vapors in gas flowing through buffer chamber 710 if the vapor concentration levels as measured by flow rate and vapor concentration measurement system 1000 exceed a certain level. Condenser 904 may include a drain configured to drain the condensed vapor. In an embodiment, condenser 904 uses UV radiation in conjunction with oxygen radicals to breakdown hydrocarbon into water and carbon monoxide, as described above.

Buffer system 750 may includes a heat exchanger 908 that is configured to adjust temperature of a gas flowing through buffer chamber 710 if temperature readings by metrology and control unit 790 indicate the temperature of the gas flowing through buffer chamber 710 is above or below a certain temperature or range of temperatures. In an embodiment, metrology and control system 790 is configured to change the temperature of gas flowing through buffer chamber 710 based on the temperature in environmental chamber 724 as measured by metrology and control system 760.

Buffer system 750 may includes a make-up gas input 910 to supply gas to buffer system 750. In an embodiment, metrology and control system 760 detects a change in gas pressure due to, for example, leakage via load lock 770. Metrology and control system 760 is configured to control make-up gas input 910 to supply gas to buffer chamber 710 based on measurements of gas pressure in buffer chamber 710.

Further, changes to the temperature and/or flow rate in the buffer chamber 710 may well have an effect on the temperature and/or flow rate in the environmental chamber 724 and/or the reflow system 740. Accordingly, changes may be made to temperature and/or flow rate of gas in the environmental chamber 724 and/or the reflow system 740 to compensate therefor.

VII. Flow Rate and Vapor Concentration Measurement System

FIG. 10 illustrates an example flow rate and vapor concentration measurement system (FRVC) 1000 according to an embodiment of the invention. FRVC 1000 includes a first transducer 1002, a second transducer 1004, a controller (e.g., control logic) 1008, temperature sensors 1014a-c, a pressure sensor 1018 and a tube 1006. Tube 1006 includes a vent 1010 and a vent 1012 to allow for ingress or egress of a gas whose vapor concentration and/or flow rate are to be measured. Transducer 1002 and transducer 1004 are each coupled to control logic 1008 and tube 1006. In an embodiment, tube 1006 may be optional with transducer 1002 and transducer 1004 being mounted directly opposite each other inside buffer system 750, reflow system 740 and/or environmental chamber 724. Controller 1008 may be control logic and these terms are used interchangeably throughout. Tube 1006 may be cylindrical as shown in FIG. 10 or alternatively may be of any other shape e.g. a square, a hexagon, etc.

In one exemplary operation, one or more acoustic signal(s) are transmitted in parallel or sequentially over a known distance between transducers 1002 and 1004, which allows for determination of vapor concentration in a gas and a flow rate of the gas flowing between transducers 1002 and 1004 based on transit time of the one or more acoustic signal(s) and a temperature of the gas.

In an embodiment, the gas whose vapor concentration and/or flow rate is to be measured flows through tube 1006. The speed of sound in tube 1006 depends on the temperature, pressure of the gas, and vapor concentration in the gas, for example as shown in the calculations below. By sending an acoustic signal over a known distance and measuring the transit time, the vapor concentration levels and flow rate are determined.

Figure 11:
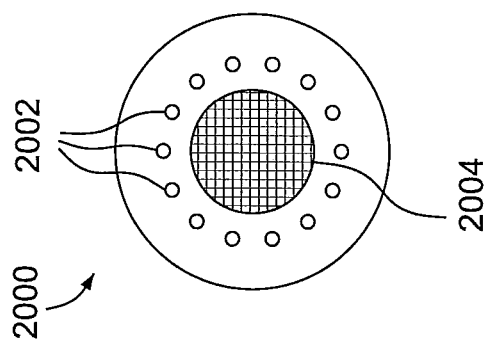
FIG. 11 illustrates an example speaker according to an embodiment of the invention.

In an embodiment, transducer 1002 is a speaker, e.g., speaker 2000 in FIG. 11, with surrounding holes 2002 to prevent a pressure difference build-up in front of and behind a wire mesh 2004. Transducer 1004 may also be a speaker, for example similar to speaker 2000, or alternatively may be a metal plate, which acts as a reflector for sound. FRVC 1000 may be used in two configurations. In the first configuration, transducer 1002 and transducer 1004 are both speakers 2000. In the second configuration, transducer 1002 is speaker 2000 and transducer 1004 is a metal plate.

In the first configuration, both transducers 1002 and 1004 can emit and receive a respective acoustic signal. The first configuration allows measurement of vapor concentration and flow rate simultaneously. The second configuration allows for a longer traveling distance of an acoustic signal, since the acoustic signal reflects from transducer 1004 and returns to transducer 1002, thereby increasing the accuracy of the measurement. However, the second configuration does not allow measurement of gas flow rate since acoustic signals from both transducer 1002 and transducer 1004 cannot be sent simultaneously.

In the first configuration, transducer 1002 and transducer 1004 can transmit respective acoustic signals in parallel or sequentially. If transmitting respective acoustic signals sequentially, transducer 1002 or transducer 1004 should not transmit when either transducer is expected to receive a signal from the other transducer. When transducer 1002 and transducer 1004 transmit respective acoustic signals simultaneously, the respective acoustic signals interfere in a region between the two transducers. This interference, however, does not affect the acoustic transit time measurement of the respective acoustic signals.

Temperature has a significant influence on the speed of sound waves or signals in a medium, and thus may be monitored by three temperature sensors 1014a-c. For example, an average temperature value may be used in calculations. In alternate embodiments, fewer or more temperature sensors 1014 may be used. Pressure of the gas is measured using pressure sensor 1018.

Control logic 1008 is configured to measure acoustic transit time between a first one of the transducers, e.g., first transducer 1002, sending an acoustic signal, and a second one of the transducers, e.g., second transducer 1004, receiving the acoustic signal. Control logic 1008 may also control first transducer 1002 and/or second transducer 1004 to transmit or receive an acoustic signal. Additionally, or alternatively, control logic 1008 receives measurement data from temperature sensors 1014a-c and pressure sensor 1018. Based on one or more of measurements of acoustic transit time and distance between transducer 1002 and transducer 1004, temperature and pressure measurements, control logic 1008 may determine vapor concentration and/or flow rate of a gas using calculations described below.

VII. a). Vapor Concentration Measurement

Conventional vapor concentration sensors can be limited to vapor concentration measurement of water vapor or of certain specific materials, and may not be universal, thereby requiring different sensors for measuring vapor concentrations of different liquids. Conventional vapor sensors are also slow, for example they may have a lag time of above one second between measurements. Furthermore, in the exemplary immersion lithography systems as described herein, evaporation of immersion liquid, such as liquid 704 in FIG. 7, causes thermal heat loads that may cause conventional vapor concentration sensors to malfunction or fail. This may especially be the case for all wet and high numerical aperture (high NA) systems. In contrast, operation of FRVC 1000 (FIG. 10) is not necessarily limited to a certain temperature range or type of vapor. In addition, conventional vapor sensors may be only able to measure vapor concentration locally and cannot measure vapor concentrations that are close to 100%.

Embodiments of FRVC 1000 in FIG. 10 presented herein can allow for measurement of vapor pressure inline over a large area in a substrate stage system (for example environmental chamber 724 in FIG. 7) or be used as a separate sensor in pipelines (for example in buffer system 750 or reflow system 740 in FIG. 7). FRVC 1000 allows for measurement of vapor concentration with a frequency of approximately 100 Hz for vapor or any type of liquid, e.g., vapor of immersion liquid 704, up to a vapor concentration of about 100%. The measurement of vapor concentration in embodiments presented herein are based on a change of sound velocity due to presence of vapor. Higher vapor concentration decreases sound velocity, while lower vapor concentration increases sound velocity.

Unlike conventional sensors, FRVC 1000 may not rely on absorption or desorption from an active surface to measure vapor concentration. As a result, a lag time for FRVC 1000 to measure vapor concentration may be determined by the rate of temperature measurements by temperature sensors 1014a-c. Rate of temperature measurements is typically about 10 Hz which is significantly faster than the rate of about 0.1 to 0.5 Hz required for absorption or desorption by conventional vapor concentration sensors. In embodiments described herein, the speed of the vapor concentration and/or flow rate measurement is only limited by the acoustic transition time, which is typically in the order of approximately milliseconds.

Example calculations to determine a percentage vapor concentration are provided below. Percentage vapor concentration is given by:

$$h_{sample} = \frac{0.01 \cdot \Omega[\%] \cdot p_{sample}}{p} \quad (1)$$

where $h_{sample}$ is vapor concentration, $p_{sample}$ is a saturation vapor pressure of the vapor in a gas, $\Omega[\%]$ is the relative concentration of the vapor in a gas, defined as the ratio between the absolute concentration of the vapor in gas and the maximum possible absolute concentration of the vapor in gas ($\Omega[\%]$ is also referred to as relative humidity if the vapor is water vapor); and p is pressure of the gas. Rewriting equation (1) gives $\Omega[/\%]$ as:

$$\Omega[\%] = 100 \cdot \frac{p}{p_{sample}} \cdot h_{sample} \quad (2)$$

To determine $\Omega[\%]$ as function of the speed of sound c, a relation between $h_{sample}$ and c is established below. Speed of sound is given by:

$$c = \sqrt{\frac{C}{\rho}} \quad (3)$$

where c is the speed of sound; C is stiffness coefficient; and $\rho$ is density of the gas. For fluids and gases there is no shear stress, only volumetric deformation and hence C=K, where K is a bulk modulus. K is given by:

$$K = \gamma \cdot p \quad (4)$$

where $\gamma$ is an adiabatic constant and p is pressure of the gas. Based on equation 4, equation 3 can be re-written as:

$$c = \sqrt{\frac{\gamma \cdot p}{\rho}} \quad (5)$$

p can be rewritten as:

$$p = \frac{nRT}{V} \quad (6)$$

where n is a mole number; R is a universal gas constant (8.3145 J/mol*K); T is absolute temperature of the gas; and V is volume of the gas (or tube 1006). $\rho$ can be re-written as:

$$\rho = \frac{nM}{V} \quad (7)$$

where M is molar mass of the gas.

Combining equation (5), (6) and (7) gives the following equation for the speed of sound:

$$c = \sqrt{\frac{\gamma \cdot nRT/V}{nM/V}} = \sqrt{\frac{\gamma RT}{M}} \quad (8)$$

For gas mixtures like air, M is the average molar mass of the constituents of the mixture. The mean molar mass of dry air ($M_{dry}$) is 28.97 g/mol. If for instance water, with a molar mass of 18.02 g/mol, evaporates into the air, the average mass is lowered and a speed of sound increases. If a sample liquid e.g., immersion liquid 704 evaporates in air, the average molar mass can be calculated by the following equation:

$$M \equiv M_{av} = M_{dry} \cdot (1 - h_{sample}) + h_{sample} \cdot M_{sample} \quad (9)$$

$$\Leftrightarrow h_{sample} = \frac{M - M_{dry}}{M_{sample} - M_{dry}}$$

where $M_{sample}$ is a molar mass of the vapor.

Relative concentration of vapor can be obtained by combining equation (2), (8) and (9):

$$\Omega[\%] = 100 \cdot \frac{p}{p_{sample}} \cdot \frac{1}{M_{sample} - M_{dry}} \cdot \left(\frac{\gamma RT}{c^2} - M_{dry}\right) \quad (10)$$

To determine Ω[%], the following parameters have to be measured: p, T and c.

Speed of sound is given by Δx/Δt where Δx is the distance between first transducer 1002 and second transducer 1004 and Δt is the time taken for an acoustic signal to travel from first transducer 1002 to second transducer 1004. $p_{sample}$, $M_{sample}$ and R are known from other measurements or are constants for a given liquid. A value of 1.40 for γ is assumed. Temperature T is measured by temperature sensors 1014a-c. Pressure sensors (not shown) are used to measure pressure p of the gas.

VII. b). Flow Rate Measurement

Conventional gas flow rate sensors require that no vapors be present in the gas. Conventional flow rate sensors are calibrated for specific gases and flow regions. Conventional flow rate sensors are also very sensitive to vapors and are easily damaged by vapors. These conventional flow rate sensors require two-phase separators to filter out liquid from the gaseous medium prior to flow rate measurement.

In contrast, embodiments of FRVC 1000 presented herein allow for flow rate measurement with or without vapors being present in the gas whose flow rate is to be measured. As described above, FRVC 1000 works for both dry and moist gas so can also be applied to water and high NA systems, for example in buffer system 750, reflow system 740 and/or environmental chamber 724. Furthermore, while conventional sensors are usually calibrated for measurement of flow rates of a specific gas, embodiments presented herein allow for measurement of flow rates for any type of gas. In addition, conventional flow rate sensors measure flow rates in specific regions. Embodiments presented herein enable measurement of flow rates inline over a large area (for example environmental chamber 724) or be used as a separate sensor in pipelines (for example in buffer system 750 or reflow system 740).

According to an embodiment, in the first configuration two acoustic signals are transmitted, one parallel to gas flow and one anti-parallel to gas flow. For example, a first acoustic signal is transmitted from first transducer 1002 and a second acoustic signal is transmitted from second transducer 1004. In this embodiment, the first and second acoustic signals are desirably transmitted simultaneously. If the gas between the transducers 1002 and 1004 is moving, i.e., if a gas flow is present, the transition times for the first and second acoustic signals will be different. The flow rate of gas is determined based on the distance between the transducers 1002 and 1004 and the velocity of both sound pulses, and a difference in transition time of pulses between transducer 1002 and transducer 1004. Example equations to calculate the flow rate are provided below.

Assuming gas flow direction being parallel to a propagation direction of the first acoustic signal:

$$c + v = \frac{\Delta x}{\Delta t_1} \quad (11)$$

where Δx is the distance between first transducer 1002 and second transducer 1004; $\Delta t_1$ is the time between sending and receiving the first acoustic signal in the direction of gas flow; v is flow rate of the gas; and c is the speed of sound. Assuming gas flow direction being opposite to a propagation direction of the second acoustic signal:

$$c - v = \frac{\Delta x}{\Delta t_2} \quad (12)$$

where $\Delta t_2$ is the time between sending and receiving the second acoustic signal against the direction of gas flow. Adding and subtracting equations 11 and 12 yields "c" and "v" as:

$$c = \frac{1}{2}\left(\frac{\Delta x}{\Delta t_1} + \frac{\Delta x}{\Delta t_2}\right) \quad (13)$$

$$v = \frac{1}{2}\left(\frac{\Delta x}{\Delta t_1} - \frac{\Delta x}{\Delta t_2}\right) \quad (14)$$

For the second configuration where first transducer 1002 is a speaker and second transducer 1004 is a reflective plate, then an average velocity is determined as:

$$c_{av} = \frac{2 \cdot \Delta x}{\Delta t} = \frac{2 \cdot \Delta x}{\Delta t_1 + \Delta t_2} \bigg\} c_{av} = \frac{2 \cdot \Delta x}{\Delta x/(c+v) + \Delta x/(c-v)} \quad (15)$$
$$= \frac{(c+v)(c-v)}{c}$$
$$= c \cdot (1 - v^2/c^2)$$

$$\Delta t_{1,2} = \frac{\Delta x}{c \pm v} \quad (16)$$

The speed of gas flow v can be determined from equation 15 and 16 above.

The application of the FRVC 1000 for flow rate measurement is not limited to dry gases and no separate two-phase separators are required to remove vapor if present.

VII. c). Acoustic Signal Transmission and Reception

As discussed briefly above, FIG. 11 illustrates an example speaker 2000 according to an embodiment of the invention. Speaker 2000 comprises wire mesh 2004 and optional holes 2002. In this embodiment, a center of wire mesh 2004 of speaker 2000 acts as an oscillator with a specific eigenfrequency. A standby voltage is applied to wire mesh 2004 in standby mode. To emit an acoustic signal, a voltage (for example 200V) is applied to wire mesh 2004. Releasing the applied voltage allows wire mesh 2004 to vibrate with its eigenfrequency and emit sound waves until the standby voltage is applied again. To receive an acoustic signal, a sound pulse impinging on wire mesh 2004 excites wire mesh 2004, thereby inducing a voltage that may be measured using, for example, control logic 1008. Holes 2002 may prevent a pressure difference build-up in front of and behind wire mesh 2004.

Figure 12:
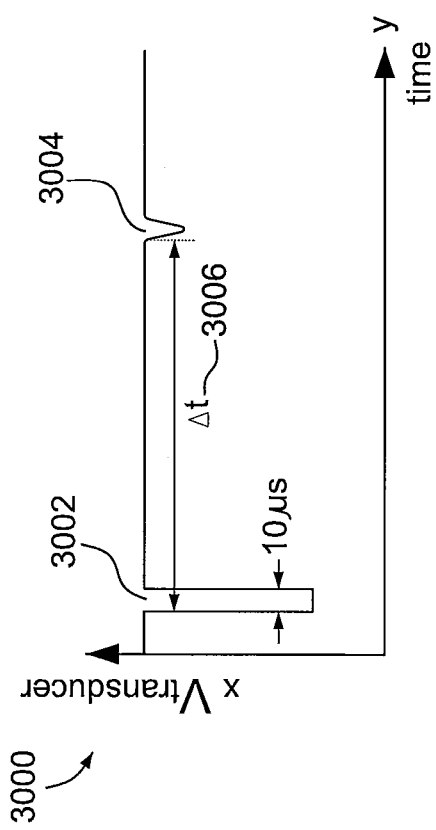
FIG. 12 shows an example graph illustrating transmission and reception of an acoustic signal according to an embodiment of the invention.

FIG. 12 shows an example graph 3000 illustrating transmission and reception of an acoustic signal. The X-axis shows elapsed time and the Y-axis shows a voltage applied to wire mesh 2004. For the first configuration, transducer 1002 emits a sound pulse 3002 and after an elapsed time period 3006, signal 3004 is received by transducer 1004. For the second configuration, transducer 1002 emits a sound pulse 3002 that reflects from transducer 1004 and after an elapsed time period (e.g. acoustic transit time) 3006, signal 3004 is received by transducer 1002.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion," respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

The terms "radiation" and "beam" used herein encompass all types of electromagnetic radiation, including ultraviolet (UV) radiation (e.g., having a wavelength of or about 365, 248, 193, 157 or 126 nm) or extreme ultraviolet radiation.

The term "lens," where the context allows, may refer to any one or combination of various types of optical components, including refractive and reflective optical components.

While specific embodiments of the invention have been described above, it will be appreciated that the invention may be practiced otherwise than as described. For example, the embodiments of the invention may take the form of a computer program containing one or more sequences of machine-readable instructions describing a method as disclosed above, or a data storage medium (e.g., semiconductor memory, magnetic or optical disk) having such a computer program stored therein. Further, the machine readable instruction may be embodied in two or more computer programs. The two or more computer programs may be stored on one or more different memories and/or data storage media.

The controllers described above may have any suitable configuration for receiving, processing, and sending signals. For example, each controller may include one or more processors for executing the computer programs that include machine-readable instructions for the methods described above. The controllers may also include data storage medium for storing such computer programs, and/or hardware to receive such medium.

One or more embodiments of the invention may be applied to any immersion lithography apparatus, in particular, but not exclusively, those types mentioned above and whether the immersion liquid is provided in the form of a bath, is confined to a localized surface area of the substrate, or is unconfined. In an unconfined arrangement, the immersion liquid may flow over the surface of the substrate and/or substrate table so that substantially the entire uncovered surface of the substrate table and/or substrate is wetted. In such an unconfined immersion system, the liquid supply system may not confine the immersion liquid or it may provide a proportion of immersion liquid confinement, but not substantially complete confinement of the immersion liquid.

A liquid supply system as contemplated herein should be broadly construed. In certain embodiments, it may be a mechanism or combination of structures that provides a liquid to a space between the projection system and the substrate and/or substrate table. It may comprise a combination of one or more structures, one or more liquid inlets, one or more gas inlets, one or more gas outlets, and/or one or more liquid outlets that provide liquid to the space. In an embodiment, a surface of the space may be a portion of the substrate and/or substrate table, or a surface of the space may completely cover a surface of the substrate and/or substrate table, or the space may envelop the substrate and/or substrate table. The liquid supply system may optionally further include one or more elements to control the position, quantity, quality, shape, flow rate or any other features of the liquid.

The immersion liquid used in the apparatus may have different compositions, according to the desired properties and the wavelength of exposure radiation used. It is intended that the term immersion liquid include other liquids, such as high refractive index liquids, e.g., fluorine containing hydrocarbons. For an exposure wavelength of 193 nm, ultra pure water or water-based compositions may be used and for this reason the immersion liquid is sometimes referred to as water and water-related terms such as hydrophilic, hydrophobic, humidity, etc. may be used, although they should be considered more generically.

In an embodiment there is an immersion lithographic apparatus, comprising: an environmental chamber, an immersion fluid handling system and an environmental conditioning system. The environmental chamber may enclose at least part of a projection system configured to project a patterned radiation beam onto a target portion of a substrate, the substrate being supported on a substrate table, and enclosing at least part of the substrate table. The immersion fluid handling system may be configured to provide an immersion fluid, comprising liquid, in the environmental chamber. The environmental conditioning system may be configured to isolate the environmental chamber from an external environment. The immersion fluid handling system may be configured to provide an inert gas substantially saturated with immersion liquid vapor to the environmental chamber as the immersion fluid.

The environmental conditioning system may be configured to regulate an atmosphere of a double walled buffer chamber surrounding the environmental chamber and/or confine immersion liquid vapor within the environmental chamber. The environmental conditioning system may be configured to regulate the atmosphere in the buffer chamber using an inert gas. The environmental conditioning system may comprise a buffer system configured to recondition and recycle the inert gas. The buffer system may comprises a blower unit. The blower unit may be configured to control flow rate of the gas through the buffer chamber based on a measurement of gas flow rate in the buffer chamber measured using a metrology and control system. The buffer system may comprise a condenser configured to condense immersion vapor present in the buffer chamber. The buffer system may comprise a drain configured to drain condensed immersion vapor. The buffer system may be configured to control temperature of gas in the buffer chamber based on a measurement of gas temperature in the buffer chamber measured using a metrology and control system.

In an embodiment the environmental conditioning system is configured to regulate a temperature of the atmosphere in the buffer chamber. The environmental conditioning system may comprise a reflow system configured to control a flow of gas through the buffer chamber and condition an atmosphere of the buffer chamber. The reflow system may be configured to remove immersion liquid vapor from the atmosphere of the buffer chamber. The double walled buffer chamber may comprise concentric buffer regions around the environmental chamber. The buffer regions may be defined at least in part by an intermediate buffer wall between the double walls.

The immersion fluid handling system may be configured to condition the atmosphere within the environmental chamber substantially to saturate the atmosphere with immersion liquid vapor. The immersion fluid handling system may comprise a gas inlet comprising a filter configured to filter gas supplied to the environmental chamber.

In an embodiment, the immersion fluid handling system has a load lock configured to access the environmental chamber. The load lock may include a gas curtain configured to separate the atmosphere of the environmental chamber from an external atmosphere and maintain the environmental conditions of the environmental chamber.

In an embodiment, the immersion fluid handling system further comprises a metrology and control system configured to monitor (i) a flow rate of gas through the environmental chamber, or (ii) a temperature of gas in the environmental chamber, or (iii) a pressure of gas in the environmental chamber, or (iv) a vapor saturation level of gas in the environmental chamber, or (v) any combination selected from (i)-(iv).

The immersion fluid handling system may further comprise a reflow system that includes a blower unit, a humidifier membrane, a condenser and a flow particle filter. The blower unit may be configured to control flow rate of gas through the environmental chamber based on a flow rate measured using the metrology and control system. The humidifier membrane may be configured to saturate the gas in the environmental chamber with immersion liquid vapor to a saturation level based on a vapor saturation measured using the metrology and control system. The condenser may be configured to condense immersion vapor in gas in the environmental chamber as a function of a saturation measured using the metrology and control system. The condenser may include a drain configured to drain condensed immersion vapor. The flow particle filter may be configured to filter gas in the environmental chamber.

The immersion fluid handling system may be configured to provide immersion liquid as the immersion fluid to a space between the projection system and the substrate or substrate table. The immersion fluid comprises an organic liquid.

In an embodiment there is a method, comprising: projecting a patterned radiation beam onto a target portion of a substrate using a projection system, the substrate being supported on a substrate table; providing an immersion fluid, comprising liquid, to an environmental chamber enclosing at least part of the projection system and enclosing the substrate or at least part of the substrate table; and isolating the environmental chamber from an external environment using an environmental conditioning system. The immersion fluid may be an immersion liquid vapor.

The method may further comprise regulating an atmosphere within the environmental chamber or confining immersion liquid vapor within the environmental chamber. The method may further comprise conditioning the atmosphere in the environmental chamber using an inert gas.

The method may further comprise reconditioning and recycling the inert gas. The method may further comprise conditioning the atmosphere in the environmental chamber to substantially saturate the atmosphere with immersion liquid vapor. The method may further comprise regulating a temperature of the atmosphere in the environmental chamber.

The method may further comprise using a load lock to access the environmental chamber. The load lock may include a gas curtain configured to separate the atmosphere of the environmental chamber from an external atmosphere and maintain the environmental conditions of the environmental chamber.

The method may further comprise using a double walled buffer chamber surrounding the environmental chamber as a buffer region between the environmental chamber and the external environment. The method may further comprise providing a flow of gas through the double walled buffer chamber using a buffer system. The buffer system may remove immersion liquid vapor from the atmosphere of the buffer chamber by condensation. The double walled buffer chamber may comprise concentric buffer regions around the environmental chamber. The buffer regions may be at least partly defined by an intermediate buffer wall between the double walls. The immersion fluid may comprise an organic liquid.

In an embodiment there is a lithographic apparatus, comprising: a substrate table; a projection system; and an environmental isolating system. The substrate table is configured to support a substrate. The projection system is configured to project a patterned radiation beam onto a target portion of the substrate. The structure is configured to provide a liquid to a space between the projection system and the substrate and/or substrate table. The environmental isolating system is configured to isolate liquid provided by the structure and vapor of the liquid from an external environment. The environmental isolating system may be configured to isolate at least part of the projection system, the structure, and/or the substrate table.

In an embodiment there is provided an immersion lithographic apparatus, comprising: a substrate table; a projection system and an environmental conditioning system. The substrate table is configured to support a substrate. The projection system is configured to project a patterned radiation beam onto a target portion of a substrate. The environmental conditioning system configured to isolate an isolated environment from an external environment. The isolated environment may comprise at least part of the projection system, and at least part of the substrate table, and to provide to the isolated environment an inert gas substantially saturated with immersion liquid vapor.

The immersion lithographic apparatus may further comprise a structure in the isolated environment. The structure may be configured to supply immersion liquid to a space between the projection system and the substrate or substrate table. The environmental conditioning system may comprise a gas handling system to provide the inert gas substantially saturated with immersion liquid vapor. The environmental conditioning system may comprise an environmental chamber to isolate the isolated environment.

In an embodiment there is a method, comprising: projecting a patterned radiation beam onto a target portion of a substrate using a projection system, the substrate being supported on a substrate table; isolating an isolated environment from an external environment, the isolated environment comprising at least part of the projection system and at least part of the substrate table; and providing an immersion liquid vapor to the isolated environment.

In an embodiment there is an immersion lithographic apparatus, comprising: a substrate table; a projection system; an environmental chamber; and a fluid handling system. The substrate table may be configured to support a substrate. The projection system may be configured to project a patterned radiation beam onto a target portion of said substrate. The environmental chamber may enclose at least part of the substrate table and at least part of the projection system. During operation the enclosed portions of the substrate table may be in contact with an immersion liquid and the environmental chamber may be isolated from an external environment. The immersion fluid handling system may be configured to provide an inert gas substantially saturated with immersion liquid vapor to the environmental chamber.

In an embodiment there us an apparatus for use in immersion lithography, the apparatus comprising: a substrate table, an environmental chamber; and an immersion fluid handling system. The substrate table may be configured to support a substrate. The environmental chamber may enclose at least a part of the substrate table, during operation the enclosed portions of the substrate table being in contact with an immersion liquid, the environmental chamber being isolated from an external environment. The immersion fluid handling system being configured to provide an inert gas substantially saturated with immersion liquid vapor to the environmental chamber.

The substrate table may be part of a drying station. The drying station and an exposure station are located in different environmental chambers. The substrate table may be configured to be used as part of an exposure station.

The substrate table may be a table in a drying station, and the external environment may include an exposure station of an immersion lithographic apparatus. The substrate table may be a substrate table of an immersion lithographic apparatus, and the external environment may include a drying station.

In an embodiment there is a system, comprising: a first transducer, a second transducer, a pressure sensor and control logic. The first transducer is configured to transmit a first acoustic signal. The second transducer is configured to receive the first acoustic signal. The temperature sensor is configured to measure a temperature of a gas between the first and second transducers. The pressure sensor is configured to measure a pressure of the gas. Control logic is configured to measure a first time period between sending and receiving the first acoustic signal and to determine a vapor concentration in the gas based on a distance between the first and second transducers, the first time period, the temperature of the gas, and the pressure of the gas.

The second transducer may be configured to transmit a second acoustic signal and the first transducer is configured to receive the second acoustic signal. The control logic may be configured to measure a flow rate of the gas based on a second time period, which corresponds to a time between sending and receiving the second acoustic signal, and the distance between the first and second transducers. The system may further comprise a tube between the first and second transducers that includes an inlet and an outlet for the gas, and that is configured to provide a path for acoustic signals to propagate between the first and second transducers. The first and second transducers may each include a wire mesh speaker. The first and second transducers may each include holes configured to prevent a pressure difference in front of and behind the wire mesh speaker. The system may be part of a metrology and control system in a lithographic apparatus. The vapor may be produced from an immersion fluid.

In an embodiment there is a system, comprising: a speaker, a metal plate, a temperature sensor, a pressure sensor and control logic. The speaker may be configured to transmit an acoustic signal. The metal plate may be configured to reflect the acoustic signal back to the speaker. The temperature sensor may be configured to measure a temperature of a gas located between the speaker and the metal plate. The pressure sensor may be configured to measure a pressure of the gas. The control logic may be configured to measure a time period between sending the acoustic signal from the speaker to be reflected from the metal plate and receiving the acoustic signal back at the speaker and to determine a vapor concentration in the gas based on a distance between the speaker and the metal plate, the time period, the temperature of the gas, and the pressure of the gas.

The system may further comprise a tube located between the speaker and the metal plate that includes an inlet and outlet for the gas, and that is configured to provide a path for acoustic signals to propagate between the speaker and the metal plate. The speaker may include holes configured to prevent a pressure difference in front of and behind the speaker. The system may be part of a metrology and control system in a lithographic apparatus. The vapor may be produced from an immersion fluid.

In an embodiment there is a method, comprising: sending a first acoustic signal from a first transducer; receiving the first acoustic signal at a second transducer; measuring a first time period between sending and receiving of the first acoustic signal; measuring a temperature of a gas between the first and second transducers; measuring a pressure of the gas; and determining a vapor concentration in the gas based on a distance between the first and second transducers, the first time period, the temperature, and the pressure of the gas.

The method may further comprise transmitting a second acoustic signal from the second transducer and receiving the second acoustic signal at the first transducer. The method may further comprise measuring a second time period between sending and receiving of the second acoustic signal. The method may further comprise determining a flow rate of the gas based on the second time period. The method may further comprise using speakers as the first and second transducers. The method may further comprise using an immersion fluid to produce the vapor.

VIII. Conclusion

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections can set forth one or more, but not all exemplary embodiments of the present invention as contemplated by the inventor(s), and thus, are not intended to limit the present invention and the appended claims in any way.

What is claimed is:

1. An immersion lithographic apparatus, comprising:
   an environmental chamber enclosing at least part of a projection system configured to project a patterned radiation beam onto a target portion of a substrate, enclosing the substrate being supported on a substrate table, and enclosing at least an edge of the substrate table;
   an immersion fluid handling system configured to provide an immersion fluid, comprising liquid and a first gas flow, in the environmental chamber, the immersion fluid handling system having an outlet to remove at least part of the first gas flow; and
   an environmental conditioning system configured to isolate the environmental chamber from an external environment, the environmental conditioning system having an inlet to provide a second gas flow, separate from the first gas flow, to interact with the first gas flow and an outlet, separate from the immersion fluid handling system outlet, to remove at least part of the second gas flow.

2. The apparatus of claim 1, wherein the immersion fluid handling system is configured to provide an inert gas substantially saturated with immersion liquid vapor to the environmental chamber as the first gas flow.

3. The apparatus of claim 1, wherein the environmental conditioning system is configured to regulate an atmosphere of a double walled buffer chamber surrounding the environmental chamber and/or confine immersion liquid vapor within the environmental chamber.

4. The apparatus of claim 3, wherein the environmental conditioning system is configured to regulate the atmosphere in the buffer chamber using an inert gas as the second gas flow.

5. The apparatus of claim 4, wherein the environmental conditioning system comprises a buffer system configured to recondition and recycle the inert gas.

6. The apparatus of claim 5, wherein the buffer system comprises a blower unit configured to control flow rate of the gas through the buffer chamber based on a measurement of gas flow rate in the buffer chamber measured using a metrology and control system.

7. The apparatus of claim 5, wherein the buffer system comprises a condenser configured to condense immersion vapor present in the buffer chamber.

8. The apparatus of claim 5, wherein the buffer system comprises a drain configured to drain condensed immersion vapor.

9. The apparatus of claim 5, wherein the buffer system is configured to control temperature of gas in the buffer chamber based on a measurement of gas temperature in the buffer chamber measured using a metrology and control system.

10. The apparatus of claim 3, wherein the environmental conditioning system is configured to regulate a temperature of the atmosphere in the buffer chamber.

11. The apparatus of claim 3, wherein the environmental conditioning system comprises a reflow system configured to control a flow of gas through the buffer chamber and condition an atmosphere of the buffer chamber.

12. The apparatus of claim 3, wherein the double walled buffer chamber comprises concentric buffer regions around the environmental chamber, the buffer regions defined at least in part by an intermediate buffer wall between the double walls.

13. The apparatus claim 1, wherein the immersion fluid handling system is configured to condition the atmosphere within the environmental chamber substantially to saturate the atmosphere with immersion liquid vapor.

14. The apparatus of claim 1, wherein the immersion fluid handling system comprises a gas inlet comprising a filter configured to filter gas supplied to the environmental chamber.

15. The apparatus of claim 1, wherein the immersion fluid handling system has a load lock configured to access the environmental chamber.

16. The apparatus of claim 1, wherein the immersion fluid handling system further comprises a metrology and control system configured to monitor (i) a flow rate of gas through the environmental chamber, or (ii) a temperature of gas in the environmental chamber, or (iii) a pressure of gas in the environmental chamber, or (iv) a vapor saturation level of gas in the environmental chamber, or (v) any combination selected from (i)-(iv).

17. The apparatus of claim 1, wherein the immersion fluid handling system is configured to provide immersion liquid as the immersion fluid to a space between the projection system and the substrate or substrate table.

18. A method, comprising:
projecting a patterned radiation beam onto a target portion of a substrate using a projection system, the substrate being supported on a substrate table;
providing an immersion fluid, comprising liquid and a first gas flow, to an environmental chamber enclosing at least part of the projection system, enclosing the substrate, and enclosing at least an edge of the substrate table;
removing at least part of first gas flow using a first outlet;
isolating the environmental chamber from an external environment using an environmental conditioning system; and
providing a second gas flow, separate from the first gas flow, to interact with the first gas flow and removing at least part of the second gas flow using a second outlet different from the first outlet.

19. The method of claim 18, further comprising regulating an atmosphere within the environmental chamber or confining immersion liquid vapor within the environmental chamber.

20. The method of claim 18, further comprising conditioning the atmosphere in the environmental chamber using an inert gas as the second gas flow.

21. The method of claim 18, further comprising conditioning the atmosphere in the environmental chamber to substantially saturate the atmosphere with immersion liquid vapor.

22. The method of claim 18, further comprising regulating a temperature of the atmosphere in the environmental chamber.

23. A lithographic apparatus, comprising:
a substrate table configured to support a substrate;
a projection system configured to project a patterned radiation beam onto a target portion of the substrate;
a structure configured to provide a liquid to a space between the projection system and the substrate and/or substrate table; and
an environmental isolating system configured to isolate liquid provided by the structure and vapor of the liquid from an external environment, the environmental isolating system comprising a double walled buffer chamber, surrounding the liquid, having an outlet into the double walls, and a buffer system to flow gas between the double walls and across the outlet from one side to another side of the outlet.

24. An immersion lithographic apparatus, comprising:
a substrate table being configured to supported a substrate;
a projection system configured to project a patterned radiation beam onto a target portion of a substrate;
an immersion fluid handling system configured to provide an immersion fluid to a space between the projection system and the substrate table;
an environmental conditioning system configured to isolate an isolated environment from an external environment using a gas flow, the isolated environment comprising at least part of the projection system, and at least an edge of the substrate table, and to provide to the isolated environment an inert gas substantially saturated with immersion liquid vapor, separate from the gas flow, to interact with the gas flow, the environmental conditioning system comprising a first outlet to remove at least part of the gas flow and a second outlet, separate from the first outlet, to remove at least part of the inert gas substantially saturated with immersion liquid vapor.

25. The immersion lithographic apparatus of claim 24, further comprising a structure in the isolated environment, the structure configured to supply immersion liquid to a space between the projection system and the substrate or substrate table.

26. A method, comprising:
projecting a patterned radiation beam onto a target portion of a substrate using a projection system, the substrate being supported on a substrate table;
isolating an isolated environment from an external environment, the isolated environment comprising at least part of the projection system and at least an edge of the substrate table, the isolating comprising providing a first gas flow and removing at least part of the first gas flow using a first outlet; and
providing an immersion liquid vapor, separate from the first gas flow, to the isolated environment to interact with the first gas flow and removing at least part of the immersion liquid vapor using a second outlet separate from the first outlet.

27. An immersion lithographic apparatus, comprising:
a substrate table configured to support a substrate;
a projection system configured to project a patterned radiation beam onto a target portion of said substrate;
an environmental chamber enclosing at least part of the substrate table and at least part of the projection system, during operation the enclosed portions of the substrate table being in contact with an immersion liquid, the environmental chamber being isolated from an external environment by a double walled buffer chamber, surrounding the environmental chamber, having an outlet into the double walls;
a buffer system to flow gas between the double walls and across the outlet from one side to another side of the outlet; and
an immersion fluid handling system configured to provide an inert gas substantially saturated with immersion liquid vapor to the environmental chamber.

28. An apparatus for use in immersion lithography, the apparatus comprising:
a substrate table configured to support a substrate;
an environmental chamber enclosing at least an edge of the substrate table, during operation enclosed portions of the substrate table being in contact with an immersion liquid, the environmental chamber being isolated from an external environment and having an inlet to provide a gas flow and an outlet remove at least part of the gas flow; and
an immersion fluid handling system configured to provide an inert gas substantially saturated with immersion liquid vapor, separate from the gas flow, to the environmental chamber to interact with the gas flow and having an outlet, separate from the gas flow outlet, to remove at least part of the inert gas substantially saturated with immersion liquid vapor.

29. The apparatus of claim 28, wherein the substrate table is part of a drying station.

* * * * *